(12) United States Patent
Eichler et al.

(10) Patent No.: US 11,699,529 B2
(45) Date of Patent: Jul. 11, 2023

(54) SYSTEMS AND METHODS FOR DIAGNOSING A STROKE CONDITION

(71) Applicant: CVAid Ltd, Tel Aviv (IL)

(72) Inventors: Nadav Eichler, Haifa (IL); Shmuel Raz, Kfar Vradim (IL); Rotem Sivan-Hoffmann, Kfar Bialik (IL); Alex Frid, Tirat-Karmel (IL); Oren Dror, Herzeliya (IL)

(73) Assignee: CV Aid Ltd, Tel Aviv (IL)

( * ) Notice: Subject to any disclaimer, the term of this patent is extended or adjusted under 35 U.S.C. 154(b) by 0 days.

(21) Appl. No.: 17/413,157

(22) PCT Filed: Dec. 11, 2019

(86) PCT No.: PCT/IL2019/051359
§ 371 (c)(1),
(2) Date: Jun. 11, 2021

(87) PCT Pub. No.: WO2020/121308
PCT Pub. Date: Jun. 18, 2020

(65) Prior Publication Data
US 2022/0044821 A1  Feb. 10, 2022

Related U.S. Application Data

(60) Provisional application No. 62/946,076, filed on Dec. 10, 2019, provisional application No. 62/908,624, (Continued)

(51) Int. Cl.
*G16H 50/30* (2018.01)
*A61B 5/00* (2006.01)
(Continued)

(52) U.S. Cl.
CPC .................................. *G16H 50/30* (2018.01)

(58) Field of Classification Search
CPC .. A61B 5/00; A61B 6/00; A61B 5/053; A61B 8/08; A61B 6/03; A61B 5/055;
(Continued)

(56) References Cited

U.S. PATENT DOCUMENTS 9,619,613 B2  4/2017  Meyer et al.
2007/0127809 A1*  6/2007  Leach .................. G06T 7/0016
382/154
(Continued)

FOREIGN PATENT DOCUMENTS

EP  3503114 A1 *  6/2019  ............. G16H 50/20

OTHER PUBLICATIONS

Eric R. Anderson, "Remote Assessment of Stroke Using the iPhone 4" Journal of Stroke and Cerebrovascular Diseases, vol. 22, No. 4 (May), 2013: pp. 340-344.
(Continued)

*Primary Examiner* — Fonya M Long
*Assistant Examiner* — Alaaeldin M Elshaer
(74) *Attorney, Agent, or Firm* — Brown Rudnick LLP; Matthew P. York

(57) ABSTRACT

A method for estimating a likelihood of a stroke condition of a subject, the method comprising: acquiring clinical measurement data pertaining to said subject, said clinical measurement data including at least one of image data, sound data, movement data, and tactile data; extracting from said clinical measurement data, potential stroke features according to at least one predetermined stroke assessment criterion; comparing said potential stroke features with classified sampled data acquired from a plurality of subjects, each positively diagnosed with at least one stroke condition, defining a positive stroke dataset; and determining, accord-
(Continued)

ing to said comparing, a probability of a type of said stroke condition, and a probability of a corresponding stroke location of said stroke condition with respect to a brain location of said subject.

52 Claims, 15 Drawing Sheets

Related U.S. Application Data filed on Oct. 1, 2019, provisional application No. 62/777,879, filed on Dec. 11, 2018.

(51) Int. Cl.
*A61B 6/00* (2006.01)
*G16H 50/20* (2018.01)

(58) Field of Classification Search
CPC .......... A61B 5/024; A61B 5/11; A61B 50/30; A61B 5/0402; G06Q 50/00; G16H 50/30; G16H 50/00; G16H 50/20; G16H 50/50; G16H 40/63
USPC ........................................ 705/2, 3
See application file for complete search history.

(56) References Cited

U.S. PATENT DOCUMENTS

| | | |
|---|---|---|
| 2013/0303900 A1* | 11/2013 | Nowinski ............. A61B 6/504 600/425 |
| 2013/0310657 A1 | 11/2013 | Sullivan et al. |
| 2015/0005645 A1 | 1/2015 | Thompson |
| 2015/0254837 A1 | 9/2015 | Goyal |
| 2016/0042123 A1* | 2/2016 | Meyer ................. A61B 5/0022 600/301 |
| 2016/0203289 A1 | 7/2016 | Grady et al. |
| 2017/0363647 A1* | 12/2017 | McPherson ........ G01N 33/6896 |
| 2018/0249967 A1* | 9/2018 | Lederman ............. G16H 50/30 |
| 2018/0279966 A1 | 10/2018 | Park et al. |

OTHER PUBLICATIONS

Pasquale Strazzullo et al. "Salt intake stroke and cardiovascular disease metaanalysis of prospective studies" BMJ: first published as 10.1136/bmj.b4567 on Nov. 24, 2009. Downloaded from http://www.bmj.com/ BMJ: first published as 10.1136/bmj. https://www.bmj.com/content/bmj/339/bmj.b4567.full.pdf.
International Search Report and Written Opinion dated Apr. 24, 2020 for International Application No. PCT/IL2019/051359 (13 pages).
Extended European Search Report issued in European Application No. 19894851.5, dated Oct. 11, 2022, 8 pages.

* cited by examiner

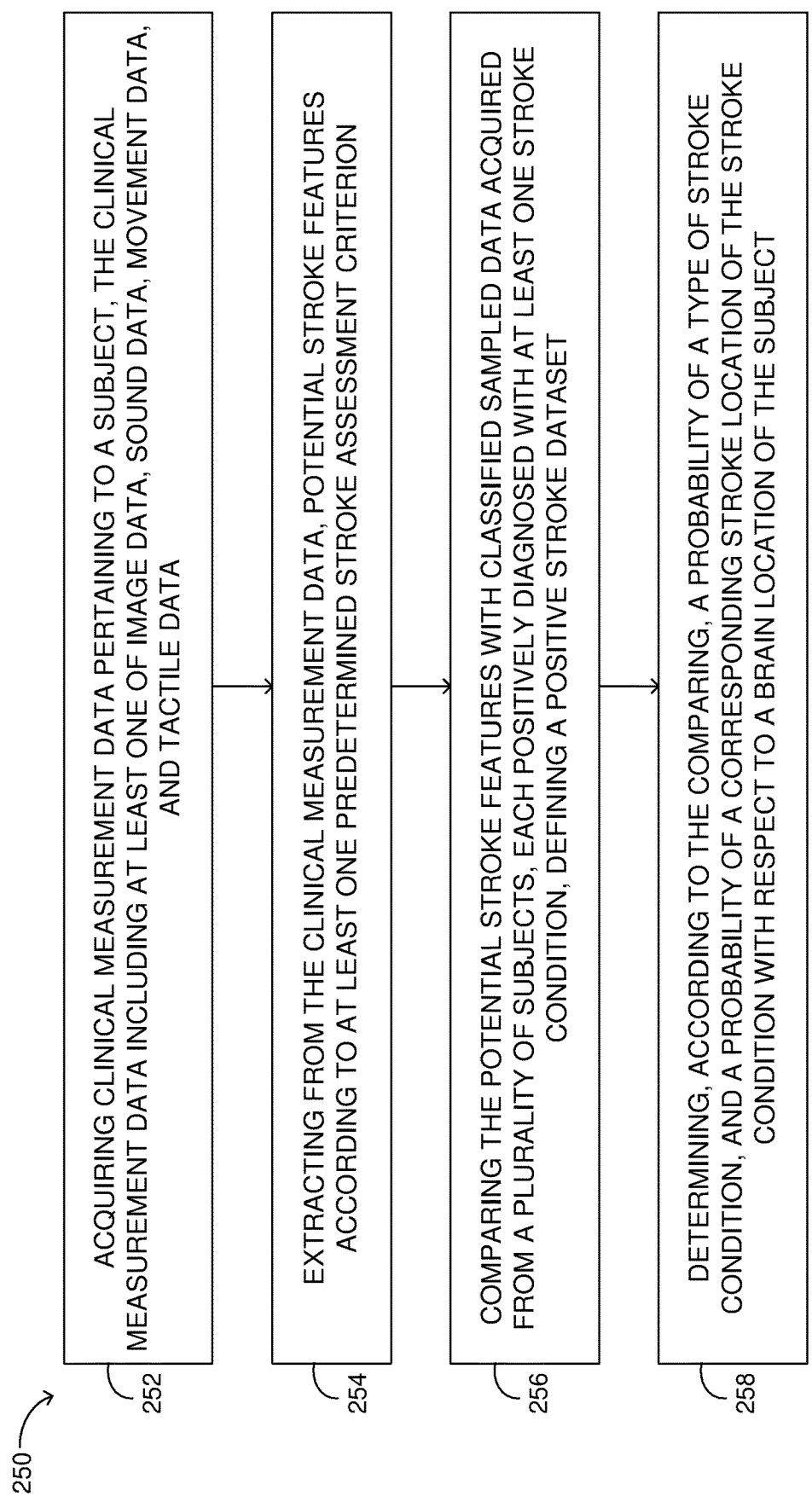

400

MANAGEMENT CONSOLE (EXAMPLE BRAIN LOCATION VIEW BEFORE BRAIN CT SCAN ACQUISITION)

STROKE LOCATION INTERPRETATION REPORT

Brain Damage Illustration

LEFT    RIGHT

Side:         Left   Right

Stroke Type:  Ischemic

LVO Location: M2

AI Statistics (Confidence)

No Stroke      21.5%

Hemorrhagic   9.3%

Ischemic M1    14.1%

Ischemic M2            55.1%

410 →
MANAGEMENT CONSOLE (EXAMPLE BRAIN LOCATION VIEW AFTER BRAIN CT SCAN ACQUISITION)
STROKE LOCATION INTERPRETATION REPORT
Brain Damage on CT scan
LEFT    RIGHT
NAVIGATE TO ESTIMATED ROI WITH CT SCAN
COLOR HIGHLIGHTS DAMAGE LOCATION
Side:          Left    Right
Stroke Type:   Ischemic
LVO Location:  M2
AI Statistics (Confidence)
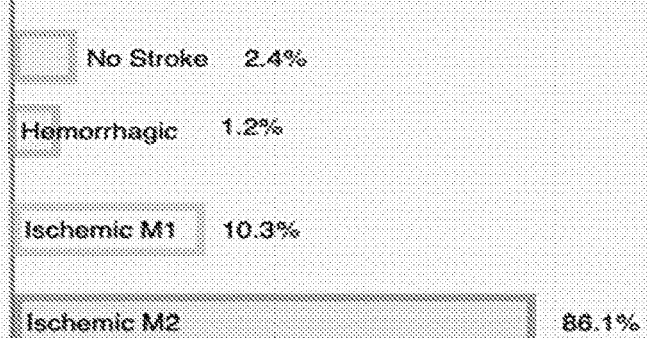
No Stroke    2.4%
Hemorrhagic  1.2%
Ischemic M1  10.3%
Ischemic M2  86.1%
FIG. 17B

SYSTEMS AND METHODS FOR DIAGNOSING A STROKE CONDITION

CROSS-REFERENCE TO RELATED APPLICATIONS

This is a national stage entry of PCT/IL2019/051359 which has an International Filing Date of Dec. 11, 2019, and which claims the benefit of and priority to U.S. Provisional Application No. 62/777,879 filed Dec. 11, 2018, U.S. Provisional Application No. 62/908,624 filed Oct. 1, 2019, and U.S. Provisional Application No. 62/946,076 filed on Dec. 10, 2019, the contents of each of which are incorporated by reference herein in its entirety.

FIELD OF THE DISCLOSED TECHNIQUE

The disclosed technique relates to systems and methods for diagnosing a medical condition, in general, and to systems and methods for diagnosing a cerebral stroke condition, in particular.

BACKGROUND OF THE DISCLOSED TECHNIQUE

A cerebral stroke or stroke for short is a cerebrovascular condition in which blood flow irregularities in the brain leads to cell death. Two main types of stroke are known, namely, ischemic and hemorrhagic. In ischemic stroke there is a deficiency or insufficiency of blood flow to cells, so as to meet the oxygen requirements, which leads to cerebral hypoxia and consequently to brain cell death also known as cerebral infarction. Blood flow irregularities may be caused by a partial or complete blockage of blood vessels or arteries and is known to be caused by several factors which include thrombus (blood clot), embolus, and stenosis (internal narrowing of a blood vessel due to atheroma also known as plaque). In hemorrhagic stroke there is intracranial bleeding (due to a blood vessel rupture, leak, aneurysm), which can lead to an increase of intracranial pressure. Since brain cells die quickly after the onset of a stroke, treatment should begin as early as possible, given that stroke is currently one of the main causes of worldwide medical-related death as well as disability. Therefore, there is a need to reduce the time to first treatment of stroke once it is detected. There are various prior art approaches that aim to reduce the time to first treatment of stroke.

U.S. Pat. No. 9,619,613 B2 issued to Meyer et al., and entitled "Device and Methods for Mobile Monitoring and Assessment of Clinical Function through Sensors and Interactive Patient Responses" is directed at a mobile assessment terminal (device) and methods for sensing and assessing a patient's responses to tests. The mobile assessment terminal includes a central processor, a memory unit, a radio, input/output units, and a touch sensitive display. The input/output units are in the form of a microphone, a speaker, a camera, and a touch sensitive display. The central processor, memory unit, input/output units, camera, and display are operationally connected to communicate. The touch sensitive display provides one or more test prompts for conducting an interactive clinical assessment of a user. Specifically, the touch sensitive display provides one or more potential responses of actions that may be performed in response to the one or more test prompts. The mobile assessment terminal receives from the user an input indicative of an action performed in response to the test prompt provided on the touch sensitive display. Following reception of sensed input via the mobile assessment terminal, the central processor processes the sensed input data by comparing it to pre-programmed standards programmable into the mobile assessment device or a central monitoring station that is in communication with the mobile assessment device, so to determine whether the sensed input is within range of normal. If the sensed input is with range of the normal, the mobile assessment terminal generates a report that is displayed to the touch sensitive display; otherwise the mobile assessment terminal generates an alarm, which is displayed on the mobile assessment terminal as well as sent to the central monitoring station.

An article entitled "Remote Assessment of Stroke Using the iPhone 4" to Anderson, Smith, Ido and Frankel, is directed at a study using hand-held technology in a tele-stroke network for evaluating the National Institutes of Health Stroke Scale (NIHSS) remotely using an iPhone 4, as well as at the bedside. The study included 20 patients with stroke being assessed by one physician at each of the patients' bedsides, while transmitting video of the patients via the iPhone to another remotely located physician whose task was to examine the patients remotely. Each physician was blinded to the other's NIHSS scores. The iPhone used a wireless Internet network to transmit video (audiovisual information) for the use of NIHSS examinations. The results of the study showed excellent agreement between remote examination and bedside examination for the majority of the NIHSS components, but moderate agreement for dysarthria, facial palsy, and gaze, and poor agreement for ataxia.

SUMMARY OF THE PRESENT DISCLOSED TECHNIQUE

It is an object of the disclosed technique to provide a novel system for estimating a likelihood of a stroke condition of a subject. The system includes a patient database ("database" for brevity), and a processor. The database contains classified sampled datasets acquired from a plurality of subjects positively diagnosed with a stroke condition, defining a positive stroke dataset. The processor is configured to receive clinical measurement data pertaining to the subject. The clinical measurement data is acquired from at least one sensor that is configured to sense at least one of image data, sound data, movement data, and tactile data pertaining to the subject. The processor is configured to extract from the clinical measurement data, potential stroke features according to at least one predetermined stroke assessment criterion. The processor is configured to compare the potential stroke features with the classified sample data in the patient database, and to determine a probability of a type of stroke condition, and a probability of a corresponding stroke location of the stroke condition with respect to a brain location of the subject.

In accordance with another aspect of the disclosed technique it is thus provided a method for estimating a likelihood of a stroke condition of a subject. The method includes acquiring clinical measurement data pertaining to the subject, extracting potential stroke features from the clinical measurement data, comparing the potential stroke features with classified sampled data, and determining, according to the comparing, a probability for a type of the stroke condition, and a probability of a corresponding stroke location of the stroke condition with respect to a brain location of the subject. The clinical measurement data includes at least one of image data, sound data, movement data, and tactile data. The extraction of potential stroke features from the clinical measurement data is according to at least one predetermined stroke assessment criterion. The classified sampled data is acquired from a plurality of subjects, each positively diagnosed with at least one stroke condition, defining a positive stroke dataset.

In accordance with a further aspect of the disclosed technique, there is thus provided a system for estimating a likelihood of a stroke condition of a subject, in which the system includes a client device enabled for communication with a remote computer. The client device includes at least one sensor, a user-interface, and a communication module. The at least one sensor is configured to acquire at least one of image data, sound data, movement data, and tactile data, all of which constitute clinical measurement data pertaining to the subject. The user-interface is configured to provide an indication of a probability for a type of the stroke condition, and a probability of a corresponding stroke location of the stroke condition with respect to a brain location of the subject. The communication module is enabled for communication with the remote computer. The communication module is configured to send the clinical measurement data to the remote computer, and to receive from the remote computer the indication. The indication is based on a comparison between potential stroke features extracted from the clinical measurement data according to at least one predetermined stroke assessment criterion, with classified sampled data in a patient database acquired from a plurality of subjects, each positively diagnosed with at least one stroke condition, defining a positive stroke dataset.

BRIEF DESCRIPTION OF THE DRAWINGS

The disclosed technique will be understood and appreciated more fully from the following detailed description taken in conjunction with the drawings in which:

FIG. 8 is a schematic diagram of a method for estimating a likelihood of a stroke condition of a subject, constructed and operative in accordance with the disclosed technique;

FIG. 17B is an exemplary screenshot of a system-generated stroke type and stroke location interpretation report that includes a brain image of a subject acquired via a neuroimaging technique superimposed with a highlighted region corresponding to the location stroke condition, after neuroimaging;

DETAILED DESCRIPTION OF THE EMBODIMENTS

Figure 1:
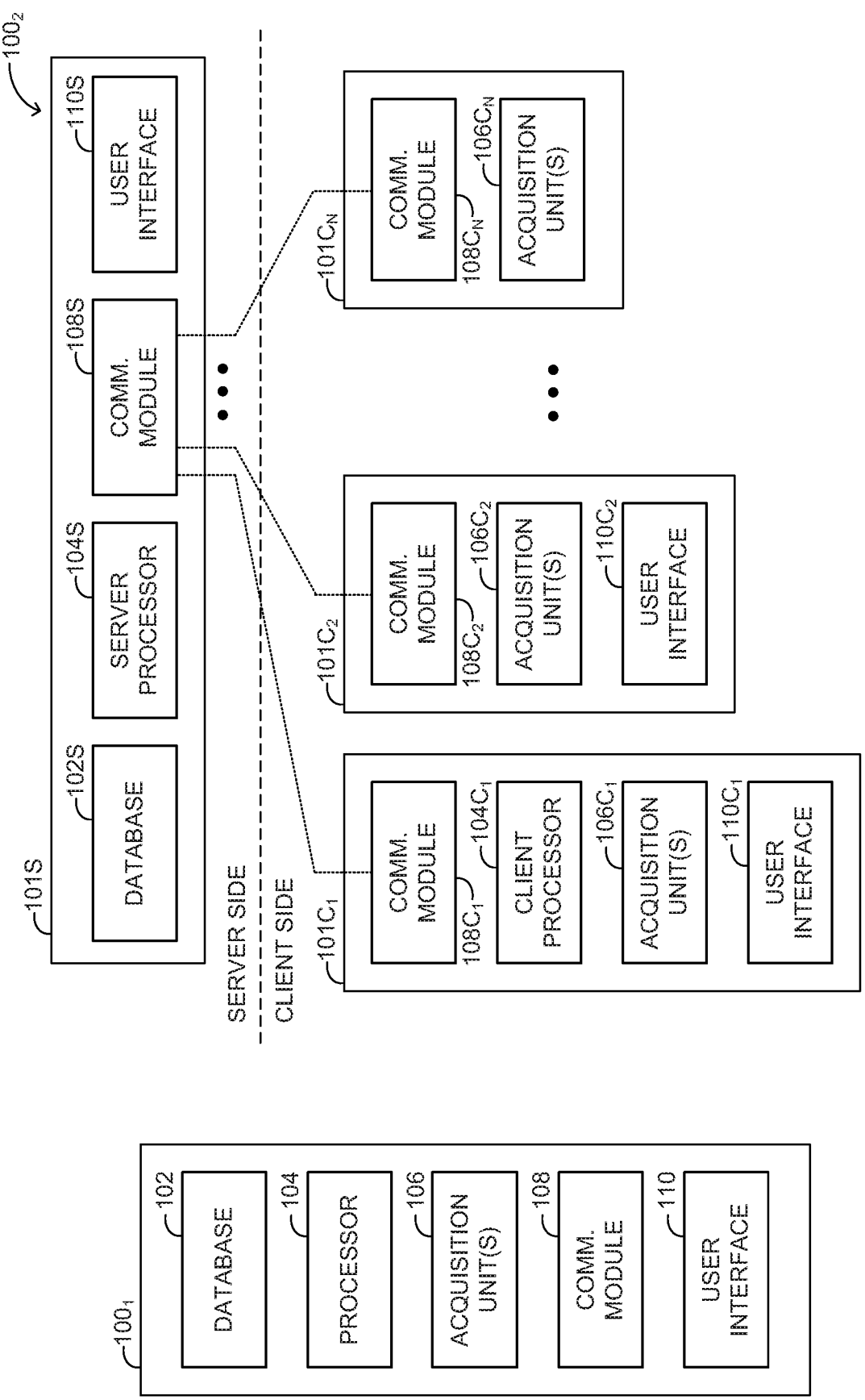
FIG. 1A is a schematic diagram illustrating a system for estimating a likelihood of a stroke condition of a subject, according to one implementation, constructed and operative in accordance with an embodiment of the disclosed technique.
FIG. 1B is a schematic diagram illustrating a system for estimating a likelihood of a stroke condition of a subject, according to another implementation, constructed and operative in accordance with an embodiment of the disclosed technique.

The disclosed technique overcomes the disadvantages of the prior art by providing systems and a method for electronically estimating a likelihood of a cerebral stroke condition (cerebrovascular accident (CVA), a "stroke" for short) of a subject (e.g., an individual, a patient). The disclosed technique allows for remote (as well as on-site) neurological and neurophysiological assessment of the subject (e.g., telemedicine via a physician) so as to allow shortening of "time to treatment" in case it was determined that the subject is suffering from a stroke condition with a high-probability (e.g., above a threshold value). The systems of the disclosed technique are configured and operative to provide an indication of a stroke as soon (i.e., immediate, in real-time) as it is detected (i.e., estimated at a high likelihood, i.e., over a threshold probability). According to one implementation, the system includes a patient database ("database" for brevity), and a processor. The patient database contains classified sampled datasets acquired from a plurality of subjects positively diagnosed with a stroke condition. The patient database may further contain classified sample datasets acquired from a plurality of subjects negatively diagnosed with a stroke condition (i.e., do not have a stroke condition). The processor is configured to receive clinical measurement data pertaining to the subject. The clinical measurement data is acquired from at least one sensor that is configured to sense at least one of image data, sound data, movement data, and tactile data pertaining to the subject. The processor is configured to extract from the clinical measurement data, potential stroke features according to at least one predetermined stroke assessment criterion (e.g., a test, a standard, a characterizing mark). The processor is configured to compare the potential stroke features with the classified sample data in the patient database, and to determine a probability for a type of stroke condition, and a probability of a corresponding stroke location of the stroke condition with respect to a brain location of the subject. The stroke location corresponds to the type of stroke for that stroke location. The brain location of the subject is an estimate that is fine-tuned by a brain image of the subject acquired, for example, by neuroimaging techniques. The brain location may be specified by the particular anatomical brain feature (e.g., blood vessel, area, etc.), as well as via three-dimensional coordinates of a brain volume with respect to reference point(s).

According to another aspect of the disclosed technique, there is thus provided a method for estimating a likelihood of a stroke condition of a subject. The method includes acquiring clinical measurement data pertaining to the subject, extracting potential stroke features from the clinical measurement data, comparing the potential stroke features with classified sampled data in a patient database potential stroke features, and determining, according to the comparing, a probability for a type of the stroke condition, and a probability of a corresponding stroke location of the stroke condition with respect to a brain location of the subject. The clinical measurement data includes at least one of image data, sound data, movement data, and tactile data. The extraction of potential stroke features from the clinical measurement data is according to at least one predetermined stroke assessment criterion. The patient database is acquired from a plurality of subjects, each positively diagnosed with at least one stroke condition, and optionally a plurality of subjects negatively diagnosed with a stroke condition.

According to a further aspect of the disclosed technique, there is thus provided a system for estimating a likelihood of a stroke condition of a subject, in which the system includes a client device enabled for communication with a remote computer. The client device includes at least one sensor, a user-interface, and a communication module. The at least one sensor is configured to acquire at least one of image data, sound data, movement data, and tactile data, all of which constitute clinical measurement data pertaining to the subject. The user-interface is configured to provide an indication of a probability for a type of the stroke condition, and a probability of a corresponding stroke location of the stroke condition with respect to a brain location of the subject. The communication module is enabled for communication with the remote computer. The communication module is configured to send the clinical measurement data to the remote computer, and to receive from the remote computer the indication. The indication is based on a comparison between potential stroke features extracted from the clinical measurement data according to at least one predetermined stroke assessment criterion, with classified sampled data in a patient database acquired from a plurality of subjects, each positively diagnosed with at least one stroke condition. The terms "stroke", "stroke event", and "stroke condition" are used interchangeably herein.

Reference is now made to FIG. 1A, which is a schematic diagram illustrating a system for estimating a likelihood of a stroke condition of a subject, according to one implementation, generally referenced $100_1$, constructed and operative in accordance with an embodiment of the disclosed technique. The following is a top-level description of the disclosed technique, which is followed by a more detailed, low-level description. FIG. 1A shows a high-level block diagram of system $100_1$, which includes a database 102, a processor 104, at least one acquisition unit 106 (also denoted interchangeably herein as "acquisition unit(s)", and in the full plural form "acquisition units"), a communication module 108 (optional), and a user interface 110 (optional). According to one implementation, system $100_1$ is a stand-alone (self-contained) device, which in itself can have several configurations. In one configuration of the standalone implementation, database 102, acquisition unit(s) 106, communication module 108, and user interface 110 are coupled (e.g., enabled for data communication) with processor 104, such that all of these elements are centralized (i.e., all components are not remote to one another), for example incorporated into a common housing (e.g., a computer station, a robot, etc.). According to another configuration of the standalone implementation, system $101_1$ is decentralized such that at least two elements selected from database 102, processor 104, acquisition unit(s) 106, communication module 108, and user interface 110 are remote to each other. In such a decentralized configuration the remote elements are enabled for communication (e.g., wired (e.g., a telephone line, etc.), wireless (e.g., Wireless-Fidelity (Wi-Fi), etc.)) with processor 104 via communication module 108 (i.e., which may also be decentralized). One example of a decentralized configuration in the standalone implementation is where acquisition unit(s) 106 is located at a particular location (e.g., a room) at a particular site (e.g., a clinic, elderly home, retirement home, etc.), while processor 104, database 102, communication module 108, and user interface 110 are located at a separate and distant location either at that site (e.g., a server room, a control room, etc.), or alternatively, at another site (e.g., a different building, etc.).

According to another implementation, system $100_1$ is a split (i.e., not standalone), in which typically both database 102, and processor 104, are separate and remote from acquisition unit(s) 106. In this typical implementation, the optional components of communication module 108 and user interface 110 are typically located with processor 104 and database 102. For example, database 102 and processor 104 are located in a cloud server (e.g., a data center, a server farm, etc.), and acquisition unit(s) 106 are dispersed at different and remote locations (e.g., different clinics). In this implementation, acquisition unit(s) 106 is/are enabled for communication with processor 104.

An overview of the block elements of system $100_1$ now follows. Generally, each acquisition unit 106 includes at least one sensor (not shown in FIG. 1A) configured to acquire data of at least one modality type, i.e., at least one of image data, sound data, movement data, and tactile data, all of which constitute clinical measurement data pertaining to a subject (e.g., individual, patient, person subject to diagnosis, and the like). Database 102 (also denoted interchangeably as "patient database") generally includes pre-classified sampled datasets acquired from a plurality of subjects positively diagnosed with at least one stroke condition, as well as pre-classified sample datasets acquired from a plurality of subjects negatively diagnosed with a stroke condition. Processor 104 is generally configured to receive the clinical measurement data pertaining to the subject, acquired from at least one sensor in each acquisition unit 106. Processor 104 is further configured to extract from the clinical measurement data, potential stroke features according to at least one predetermined stroke assessment criterion (e.g., test, characteristic, attribute), and to compare the potential stroke features with pre-classified sample data in the patient database 102 at least one of positively and negatively diagnosed with a stroke condition. Processor 104 is configured to determine a probability for a type of stroke condition, and a probability of a corresponding stroke location of the stroke condition with respect to a brain location of the subject. User interface 110 includes at least one user interface, and more typically two user interfaces: (1) a management user interface that is typically embodied as a human-machine-interface (HMI) configured to interface between system $100_1$ and a manager of system $100_1$ (e.g., a system administrator, a data scientist, a manager, a medical professional, an operator of system $100_1$, and the like), and (2) a subject or patient user interface that is embodied in the form of a HMI configured to interface between system $100_1$ and the patient that is the subject of the diagnosis. User interface 110 is generally further configured to provide an indication of a these probabilities (i.e., type of stroke condition, and probability of a corresponding location (area, region, volume) of the stroke condition with respect to a brain area of the subject). User interface may be implemented as a human-machine interface (HMI) that may have various user-interfacing layers/modalities/interfaces such as visual (e.g., implemented in hardware and software as a screen, touchscreen), auditory (e.g., a speaker), voice/verbal (e.g., a microphone), tactile (e.g., touchscreen, keyboard), movement/gesture (e.g., accelerators and gyroscopes), and the like. Communication module 108 is generally configured to enable: (1) communication between the elements of system $100_1$ (e.g., acquisition unit(s) 106 being remote from processor 104); (2) enable communication of system $110_1$ with a system administrator thereof (manager, operator, and the like); and (3) enable communication of system $100_1$ with remotely located medical professionals, hospitals, a stroke prevention and recovery center (SPARC), and the like.

According to another implementation of the disclosed technique, there is provided a system that is configured and operative in accordance with server-client architecture. To further explicate the particulars of this implementation, reference is now made to FIG. 1B, which is a schematic diagram illustrating a system for estimating a likelihood of a stroke condition of a subject, according to another implementation, generally referenced $100_2$, constructed and operative in accordance with an embodiment of the disclosed technique. System $100_2$ includes a server 101S at a "server side", and a plurality of clients $101C_1, 101C_2, \ldots, 101C_N$ (where N is an positive integer) at a "client side".

Server 101S (also denoted interchangeably herein as "server computer") and plurality of clients $101C_1, 101C_2, \ldots, 101C_N$ (also denoted interchangeably herein (in singular form) as "client computer", "client device", "client", and "user device") are enabled for communication with each other via a communication medium (e.g., a computer network, an intranet, the Internet, etc.). On the server side, server computer 101S includes a database 102S, a server processor 104S, communication module 108S, and a user interface 110S. Database 102S, communication module 108S, and user interface 110S are configured to be communicatively coupled with server processor 104S. Each component in server computer 101S may be implemented by distinct sub-components (e.g., server processor 104S may include a plurality of distinct processors, cores, etc.). In another example, database 102S is split into two or more sub-databases, i.e., a "positive-diagnosis" sub-database containing sampled datasets acquired from a plurality of subjects positively diagnosed with at least one stroke condition, and a "negative-diagnosis" sub-database containing sampled datasets acquired from a plurality of subjects negatively diagnosed with a stroke condition.

On the client side, there are generally N clients, where each i-th client device ($1 \leq i \leq N$; $i \in \mathbb{Z}$) includes at least one acquisition unit $106C_i$ and a communication module $108C_i$. Each i-th client device may further include optionally, a client processor $104C_i$ and a user interface $110C_i$. Additionally, client devices $101C_1, 101C_2, \ldots, 101C_N$ may typically further include a memory device (not shown) for storing data acquired by acquisition unit(s). FIG. 1B shows several examples of different types of client devices. Client device $101C_1$ includes a client processor $104C_1$, at least one acquisition unit $106C_1$, a communication module $108C_1$, and a user interface $110C_1$. Client device $101C_2$ includes at least one acquisition unit $106C_2$, a communication module $108C_2$, and a user interface $110C_2$. Client device $101C_N$ includes at least one acquisition unit $106C_N$, and a communication module $108C_N$. Client devices $101C_1, 101C_2, \ldots, 101C_N$ are enabled for communication with server 101S via their respective communication modules. Specifically, communication module $108C_1$ of client device $101C_1$ is enabled for communication with communication module 108S of server 101S. Communication module $108C_2$ of client device $101C_2$ is enabled for communication with communication module 108S, and so forth to client device $101C_N$. Client devices $101C_1, 101C_2, \ldots, 101C_N$ may be embodied for example, in the form of smartphones, tablets, laptop computers, desktop computers, wearable devices (e.g., smart watches), "intelligent virtual assistant" (IVA) devices, "intelligent personal assistant" (IPA) devices, computerized home systems, and the like. Processors 104 and 104S are hereinafter referred interchangeably according to applicability to the implementations of FIG. 1A and FIG. 1B, respectively.

Figure 2:
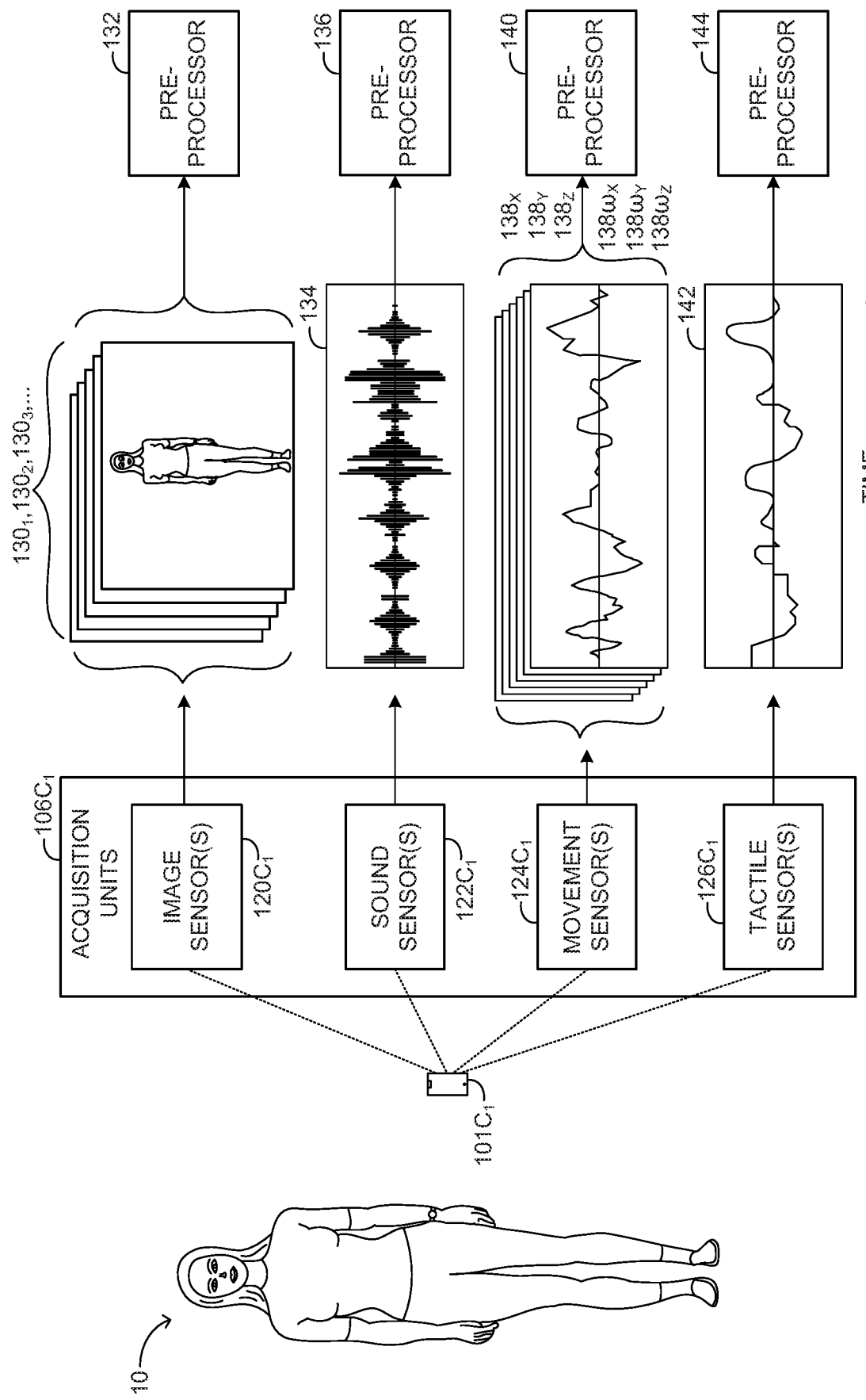
FIG. 2 is a schematic illustration of the acquisition of clinical measurement data from a subject, by a plurality of different types of sensors, constructed and operative in accordance with the embodiment of the disclosed technique.

Reference is now made to FIG. 2, which is a schematic illustration of the acquisition of clinical measurement data from a subject, by a plurality of different types of sensors, constructed and operative in accordance with the embodiment of the disclosed technique. FIG. 2 shows a subject 10 (i.e., individual, patient) who is a subject of diagnosis via system $100_2$ (FIG. 1B) of the disclosed technique. The principles described herein likewise apply to system $100_1$ (FIG. 1A), with respect to acquisition units 106. Client device $101C_1$ includes a plurality of acquisition units: image sensor(s) $120C_1$ (camera(s)), sound sensor(s) $122C_1$, movement sensor(s) $124C_1$, and tactile sensor(s) $126C_1$. A plurality of different sensor types are shown for the purpose of example, though only one sensor of one type may be sufficient to estimate a likelihood of a stroke condition of subject 10. Alternatively, a plurality of sensors of the same type may be sufficient. To enhance the estimation result, the system of the disclosed technique typically employ a plurality of different sensor types as such sensors are ubiquitous in many user devices (e.g., smartphones, smart wearable devices (e.g., watches), and the like). Additionally and optionally, a blood pressure measurement device (not shown) may be used as to acquire clinical measurement blood pressure data (not shown).

Prior to the process of estimating a likelihood of a stroke condition, subject 10 (or via an intermediary thereof) is usually required to set-up a user account on server 101S via client device $101C_1$ that is enabled for this purpose. Typically, subject 10 (or via an intermediary thereof) may be required to input her/his identifying information into client device $101C_1$ that is configured and operative to run software (e.g., an application, a program that may be downloaded to the client device, be pre-installed on the client device, etc.) and enabled for communication and the exchange of data with server 101S (FIG. 1B). Subject 10 may be typically required to register with system $100_2$ of the disclosed technique prior to use (e.g., via client device $101C_1$, or alternatively via any other capable device, service operator, etc.). This step is denoted herein as an "initial set-up" stage. Identifying information may include the subject's name, age, sex, as well as auxiliary information that may provide additional cues in the estimation of a likelihood of a stroke condition. Auxiliary information may include medical information (e.g., current and/or previous stroke data such as stroke type (e.g., ischemic, hemorrhagic), as well as hypertension, current and previous heart disease/conditions (e.g., atrial fibrillation), blood cholesterol data, diabetes mellitus, etc.), as well as lifestyle-related information (e.g., known risk factors such as tobacco smoking, obesity, etc.). While auxiliary information may be beneficial to the estimation result, such information is not necessary for the disclosed technique to produce accurate results. Client device $101C_1$ is configured to receive via at least one of user interface $110C_1$ (FIG. 1B) and acquisition units $106C_1$ the subject's identifying information as well as the auxiliary information and to send these to server 101S via communication module $108C_1$.

Following the initial set-up stage, the system and method of the disclosed technique are configured and operative to acquire and construct at least one baseline profile of subject 10. The baseline profile defines a time-dependent state of that subject's detected neurological state (i.e., a personalized profile) that includes an estimation to a likelihood of a stroke condition at a particular time. The disclosed technique employs a plurality of baseline profiles that are time-stamped, recorded and stored in database 102. The baseline profiles may be acquired and recorded on a timely basis (e.g., in a scheduled manner), on an initiation/prompt basis (e.g., patient initiated, medical professional initiated, third-party initiated (e.g., by a family member, relative, etc.), on the basis of measurements indicators triggers, a non-scheduled manner, and the like. Should the baseline profile of a particular individual be indicative of a high likelihood of a stroke condition (i.e., with respect to a particular threshold), systems $101_1$, and $101_2$ are configured and operative to alert the user, the user's relatives, and medical professionals, as will be detailed hereinbelow. Attaining a current estimation of a likelihood of a stroke condition (which can serve as a time-stamped baseline profile) is facilitated by acquiring clinical measurement data via the acquisition units. According to one implementation, the acquirement of the clinical measurement data involves prompting subject 10 to follow instructions, directions or guidance, provided by user interface $110C_1$ (e.g., via a program installed in client device $101C_1$, via a phone call, an Internet website, etc.). According to another implementation, clinical measurement data is acquired automatically, with or without user intervention. The baseline profile enables systems $100_1$ and $100_2$ to monitor, detect, and alert to changing trends in the clinical measurement data (e.g., speech irregularities get progressively worse, etc.), so as to facilitate early estimation and detection of a stroke condition before it occurs (upcoming stroke event). Furthermore, the baseline profile enables systems $100_1$ and $100_2$ to compare different baseline profiles (amongst themselves) of a particular subject acquired at different times (e.g., current baseline profile as well as past baseline profiles) and generate respective comparison reports (i.e., between at least two different baseline profiles).

Prior to use, systems $101_1$ and $101_2$ are configured (e.g., via a program, software, hardware configuration, firmware configuration, algorithm, self-modifiable program, or combinations thereof) (also denoted herein as "pre-configured") or trained (i.e., via machine learning (ML) techniques, such as machine learning classification/classifier (MLC)) (also denoted herein as "pre-trained") so as to be enable to classify input data (e.g., distinguish, identify) among two main classes of potential stroke features stored in two different and main datasets, namely, a positive stroke dataset, and a negative stroke dataset. The positive stroke dataset includes a plurality of entries (labeled data) that are sampled from individuals positively diagnosed with at least one stroke condition. The negative stroke dataset includes a plurality of entries that are sampled from individuals negatively diagnosed for a stroke condition (i.e., are verified not to have a stroke condition). Given a tested potential stroke feature input, systems $101_1$ and $101_2$ are configured and/or trained to classify, i.e., associate the input potential stroke feature with either one of the positive stroke dataset (with a particular probability of match), the negative stroke dataset (with a particular probability of match), or (untypically) be indeterminate (i.e., neither). The configuration or training is achieved at different hierarchies (i.e., types and levels of data), from the data type to a particular attribute in the data, such as per clinical measurement type (e.g., image data, sound data), per sub-type (e.g., image feature, sound feature), and so forth according to the resolution required. Following the initial configuration or training phase, systems $101_1$ and $101_2$ are enabled for "steady-state" operation. The MLC is trained on dataset entries that may include data pertaining or based on computer tomography (CT) scans marked and evaluated by a trained physician, as well as digital reports of subjects and their respective image data, sound data, movement data, and tactile data, and optionally, blood pressure data.

Image sensor $120C_1$ in client device $101C_1$ is typically part of a camera system assembly configured and operative to acquire image data 130 usually in the form of at least one image, and typically a plurality of images $130_1$, $130_2$, $130_3$, . . . of at least a part of subject 10 (e.g., face, torso and face, entire body, etc.). Images $130_1$, $130_2$, $130_3$ may be outputted as individual still images, as well as in the form of video. The camera system assembly may employ a plurality of individual camera modules each having its own image sensor, lens, and image software. The camera system may further be augmented by employing range imaging techniques (not shown) that capture depth information (i.e., distance between points in an external scene with respect to at least one reference point (e.g., the sensor's image plane)) that may be presented as a two-dimensional (2-D) range image. Such techniques include for example, time-of-flight (ToF) techniques, structured light techniques, stereophotogrammetry techniques, interferometry techniques, and the like. Images $130_1$, $130_2$, $130_3$, ... are inputted into a preprocessor 132 that is configured and operative to preprocess the images by various techniques that include for example, image cropping, scaling, correction of distortions, isolation of image background from image foreground, color adjustment, exposure adjustment, sharpening, removal of noise, edge detection, etc. Image preprocessing may typically be performed but is optional.

Sound sensor $122C_1$ (e.g., a microphone) in client device $101C_1$ is configured and operative to acquire sound produced by subject 10 (i.e., typically voice, speech, and the like) and to produce corresponding sound data 134 that is graphically represented in FIG. 2 as a sound waveform (shown as a variation of amplitude in the time domain). Alternatively, sound data is in a frequency domain (i.e., an amplitude value for each frequency in the frequency range of sound sensor $112C_1$). Sound sensor $112C_1$ outputs sound data 134 to a preprocessor 136 that is configured and operative to preprocess sound data 134 by various techniques, which include for example, equalization, frequency band-pass filtering, level compression, noise reduction, etc. Sound preprocessing may typically be performed but is optional. Sound data may be multi-dimensional (not shown) (e.g., stereo sound data). Movement sensors $124C_1$ is typically embodied as at least one of a multi-axis accelerometer (e.g., tri-axis for X, Y, Z Cartesian axes) that is configured to measure acceleration for each axis and to produce a multi-dimensional accelerometer output $138_X$, $134_Y$, and $138_Z$ in the time domain for each axis, as well as a multi-axis gyroscope that is configured to measure rotational velocity (i.e., roll, pitch, and yaw) and to produce a multi-dimensional gyroscope output $138\omega_X$, $138\omega_Y$, and $138\omega_Z$ for each axis. Movement sensors $124C_1$ may further include magnetometers. The outputs (signals) of the movement sensors $124C_1$ are inputted into a preprocessor 140 that is configured and operative to preprocess data from multi-axis accelerometers as well as multi-axis gyroscopes by various techniques, which include for example, noise reduction, filtering, etc. Movement data preprocessing may typically be performed but is optional. Tactile sensor $126C_1$ may be embodied as a touchscreen of client device $101C_1$, a pressure sensor, an electrical resistance/conductivity sensor (for measuring an electrodermal response), and the like that is configured and operative to measure and produce tactile data 142 in the time domain acquired from subject 10. Tactile data 142 is inputted into a processor 144 that is configured and operative to preprocess data by various techniques, which include, noise reduction, filtering, etc. Tactile data preprocessing may typically be performed but is optional. Preprocessors 132, 136, 140, 144, in general, are configured to respectively preprocess image data 130, sound data 134, movement data 138, and tactile data 142 via signal processing techniques and algorithms (e.g., filtering, error correction, etc.). Preprocessors 132, 136, 140, and 144 are implemented in hardware, software, or both, and may be discrete components or integrated into one processor.

Systems $100_1$ and $100_2$ enable sensor fusion of the acquired clinical measurement data from the acquisition units (also denoted herein as "multi-modal" data defined as clinical measurement data that is acquired from different types of sources (e.g., sensors)) in the temporal domain as well as in the spatial domain so as allow for more accurate results than clinical measurement data acquisition from a single modality (i.e., one source type, e.g., image data) (e.g., by using Kalman filtering, and the like). Sensor fusion may be complete (i.e., data fused or combined from all data source types or modalities), or alternatively, may be partial (i.e., "partial sensor fusion") where data is not fused or combined from all data source types.

After acquiring the clinical measurement data from the acquisition units (i.e., the multi-modal), systems $100_1$ and $100_2$ are configured and operative to extract potential stroke features (e.g., attributes and their corresponding value) from the clinical measurement data, according to at least one predetermined stroke assessment criterion. A predetermined stroke assessment criterion is any characterizing mark, trait, standard, or rule for evaluating, assessing, deciding, or testing a likelihood to a presence of a stroke condition.

Figure 3:
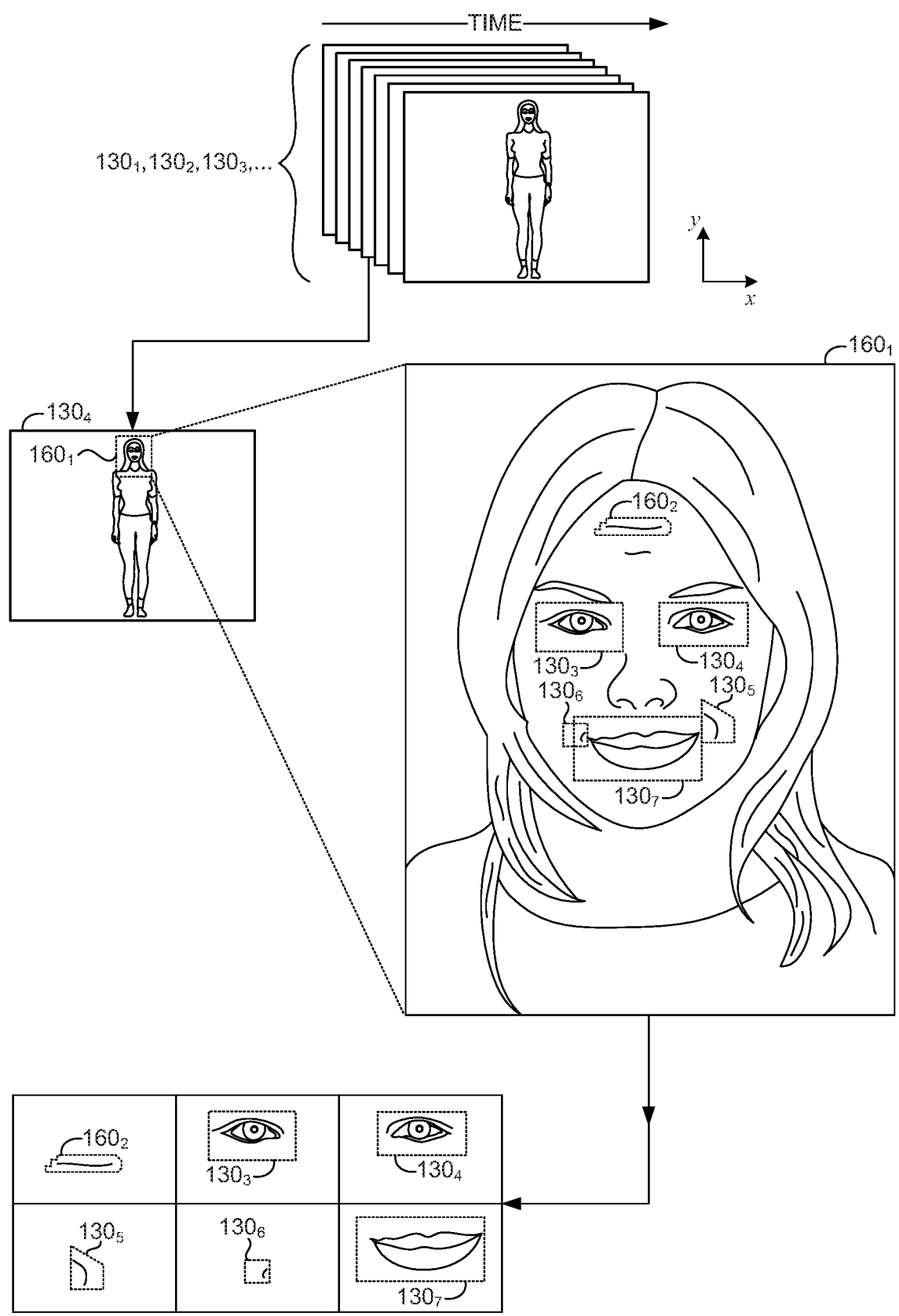
FIG. 3 is a schematic illustration of an example extraction of potential stroke features from clinical measurement image data, according to the disclosed technique.

Reference is now further made to FIG. 3, which is a schematic illustration of an example extraction of potential stroke features from clinical measurement image data, according to the disclosed technique. FIG. 3 shows time-sequential images $130_1$, $130_2$, $130_3$, ... constituting acquired clinical measurement image data 130 of subject 10. Each of processor 104 (FIG. 1A) and server processor 104S (FIG. 1B) is configured and operative to extract potential stroke features from the clinical measurement image data. The process of extraction involves selection and isolation, and is operative in both the time domain, as well as in the spatial domain. Specifically, in the time domain, extraction involves selection and isolation of at least one image (frame) captured at a particular point in time, or a plurality of images captured at distinct points in time (or time range(s)). An extracted image is denoted herein as a point of interest (POI) in time, or "time POI" for brevity. A plurality of images captured at a particular time range is denoted herein as a region of interest (ROI) in time, or "time ROI" for brevity. Particularly for the spatial domain, extraction involves selection and isolation of at least one part in an image (i.e., a pixel having an associated spatial location (e.g., an (x, y) coordinate in the image), or group of pixels each having their respective spatial locations). Each extracted pixel from an extracted image is denoted herein as a POI in the spatial domain, or for brevity "spatial POI". A plurality of extracted contiguous group of pixels is an image object denoted herein as a ROI in the spatial domain, or "spatial ROI" for brevity. In the example of FIG. 3, processors 104 and 104S extract a time POI, i.e., image $130_4$, with respect to images $130_1$, $130_2$, $130_3$, ..., i.e., as well as a spatial ROI $160_1$ (i.e., the captured image of the head of subject 10). The process of spatial ROI extraction may involve image segmentation techniques. Spatial ROI $160_1$ may include at least one nested spatial ROI, which is a ROI within a ROI (i.e., a partial ROI within a master ROI). As diagrammatically shown in FIG. 3, spatial ROI $160_1$ includes nested spatial ROIs $160_2$ (a forehead wrinkle of subject 10), $160_3$ (right eye), $160_4$ (left eye), $160_5$ (a left side smile wrinkle), $160_6$ (a right side smile wrinkle), and $160_7$ (lips). Alternatively, processors 104 and 104S are configured and operative to extract spatial ROIs $160_2$, $160_3$, $160_4$, $160_5$, $160_6$, and $160_7$ such that they don't constitute nested spatial ROIs (i.e., directly from image $130_4$). The extraction of features, i.e., spatial ROIs $160_2$, $160_3$, $160_4$, $160_5$, $160_6$, and $160_7$ by processors 104 and 104S is generally performed according to at least one predetermined stroke assessment criterion, as defined hereinabove.

Figure 4:
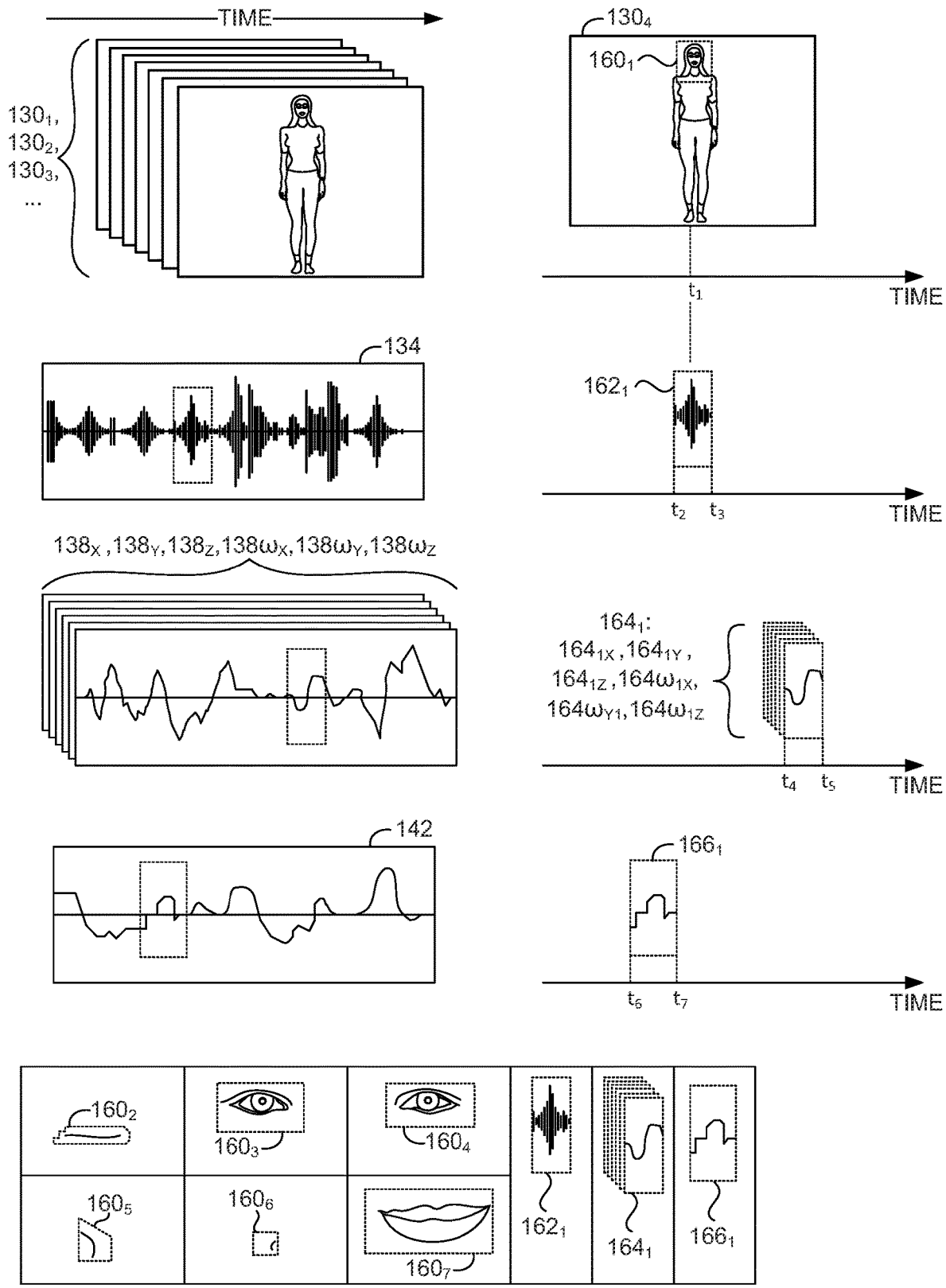
FIG. 4 is a schematic illustration showing examples of the extraction of potential stroke features from various types of clinical measurement data at various times, according to the disclosed technique.

FIG. 3 shows an example of extraction of potential stroke features from clinical measurement image data, for the purposes of explicating the disclosed technique. Extraction of potential stroke features from other types of clinical measurement data is likewise applicable according to the principles of the disclosed technique. Reference is now further made to FIG. 4, which is a schematic illustration showing examples of the extraction of potential stroke features from various types of clinical measurement data at various times, according to the disclosed technique. FIG. 4 shows the extraction of potential stroke features from image data 130 (images $130_1$, $130_2$, $130_3$, ...) (as detailed in FIG. 3), as well as sound data 134 in the time domain, movement data $138_X$, $134_Y$, $138_Z$, $138\omega_X$, $138\omega_Y$, $138\omega_Z$ in the time domain, and tactile data 142 in the time domain. Processors 104 and 104S are configured and operative to extract potential stroke features in image data 130, i.e., POI image $130_4$ in the time domain, denoted herein as time $t_1$ (or simply "$t_1$"), as well as spatial features within image $130_4$, namely, spatial ROIs $160_2$, $160_3$, $160_4$, $160_5$, $160_6$. Furthermore, processors 104 and 104S are configured and operative to extract potential stroke features in sound data 134 denoted as ROI $162_1$ in the time domain transpiring between $t_2$ and $t_3$ (along a time axis, where $t_2<t_3$), potential stroke features in movement data 138 denoted as multi-dimensional ROI $164_1$ (i.e., that includes $164_{1X}$, $164_{1Y}$, $164_{1Z}$, $164_1\omega_X$, $164_1\omega_Y$, $164_1\omega_Z$ in the time domain transpiring between time $t_4$ and $t_5$, as well as potential stroke features in tactile data 142 denoted as ROI $166_1$ in the time domain transpiring between time $t_6$ and $t_7$.

The extraction of potential stroke features from different types of clinical measurement data (i.e., acquired from different sources (e.g., sensors) of data, i.e., "multi-modal data") may time-wise correspond to each other (i.e., be synchronized in time), may overlap in time (at least partially or fully), or may be mutually exclusive in time. The example in FIG. 4 shows that POI image $130_1$ acquired at $t_1$ is included in a time range [$t_2$,$t_3$] between $t_2$ and $t_3$ (i.e., $t_2 \le t_1 \le t_3$). This indicates that extracted potential stroke features $160_2$, $160_3$, $160_4$, $160_5$, and $160_6$ from image data 130 coincide in the time range [$t_2$,$t_3$] with extracted potential stroke feature $162_1$ extracted from sound data 134. According to another example in FIG. 4, extracted potential stroke features $164_1$ do not coincide in time with extracted potential stroke feature $166_1$, although these extracted features may be linked to a common potential stroke event whose likelihood is estimated by the disclosed technique. The disclosed technique may employ correlation, as well as cross-correlation techniques to assess a statistical relationship between multi-modal data that occur in proximity to each other (e.g., within a particular time range) possibly interrelated to a common potential (suspected) stroke event, also denoted herein as "cerebrovascular accident" (CVA).

The POIs and ROIs (in the time and spatial domains) are extracted according to least one predetermined stroke assessment criterion (typically a plurality of individual criteria) that may be: (1) a standardized test (e.g., the National Institutes of Health Stroke Scale (NIHSS), the face-arm-speech-time (FAST) test, the $ABCD^2$ score, the $CHADS_2$ score and its refinement the $CHA_2DS_2VASc$ score (calculates stroke risk for subjects with non-rheumatic atrial fibrillation ("AF" or "A-fib") (early stage diagnosis), Los Angeles Pre-hospital Stroke Screen (LAPSS) test, etc.); (2) a non-standardized test; (3) a modified test based on a standardized test (e.g., a modified NIHSS (mNIHSS); (4) a customized test based on a standardized test (e.g., NIHSS), where the customized version doesn't necessarily include all sub-tests of the standardized test, and may include variations of sub-tests, as well as additional sub-tests, etc.); and (5) at least one characterizing mark or trait that can serve as a direct and/or indirect possible indication in the assessment of the likelihood of a stroke condition (e.g., a determined statistical correlation between clinical measurement data and likelihood to a stroke condition). Systems $100_1$ and $100_2$ are configured and operative to run a computerized version of each selected stroke assessment test (whether standardized or non-standardized). Tables 1-12 hereinbelow show examples of predetermined stroke assessment criteria based on NIHSS, a computerized version of which according to the disclosed technique is denoted interchangeably herein as "modified NIHSS" (mNIHSS), and "adopted NIHSS". As aforementioned, the extraction of clinical measurement data by the acquisition units may be with user intervention (e.g., prompting the subject to perform instructions, such as raising hands, speaking, etc.), be without user intervention (e.g., automatic), or be hybridized between (partial) user intervention and (partial) user non-intervention.

In the alternative implementation, the acquirement of clinical measurement data is achieved without user (subject) intervention (i.e., non-interactive approach), for example automatically, by monitoring the subject's normal activities (e.g., during walking, sitting, standing, talking, during computer use, smartphone use, etc.). Systems $101_1$ and $101_2$ acquire the clinical measurement data and extract potential stroke features from the acquired clinical measurement data without prompting the user to perform tasks required for standardized tests (e.g., NIHSS) or other types of user interactive tests. This implementation may typically employ machine learning techniques for modeling the user's various routine activities via training data that is inputted into and/or acquired by systems $101_1$ and $101_2$.

Figure 5:
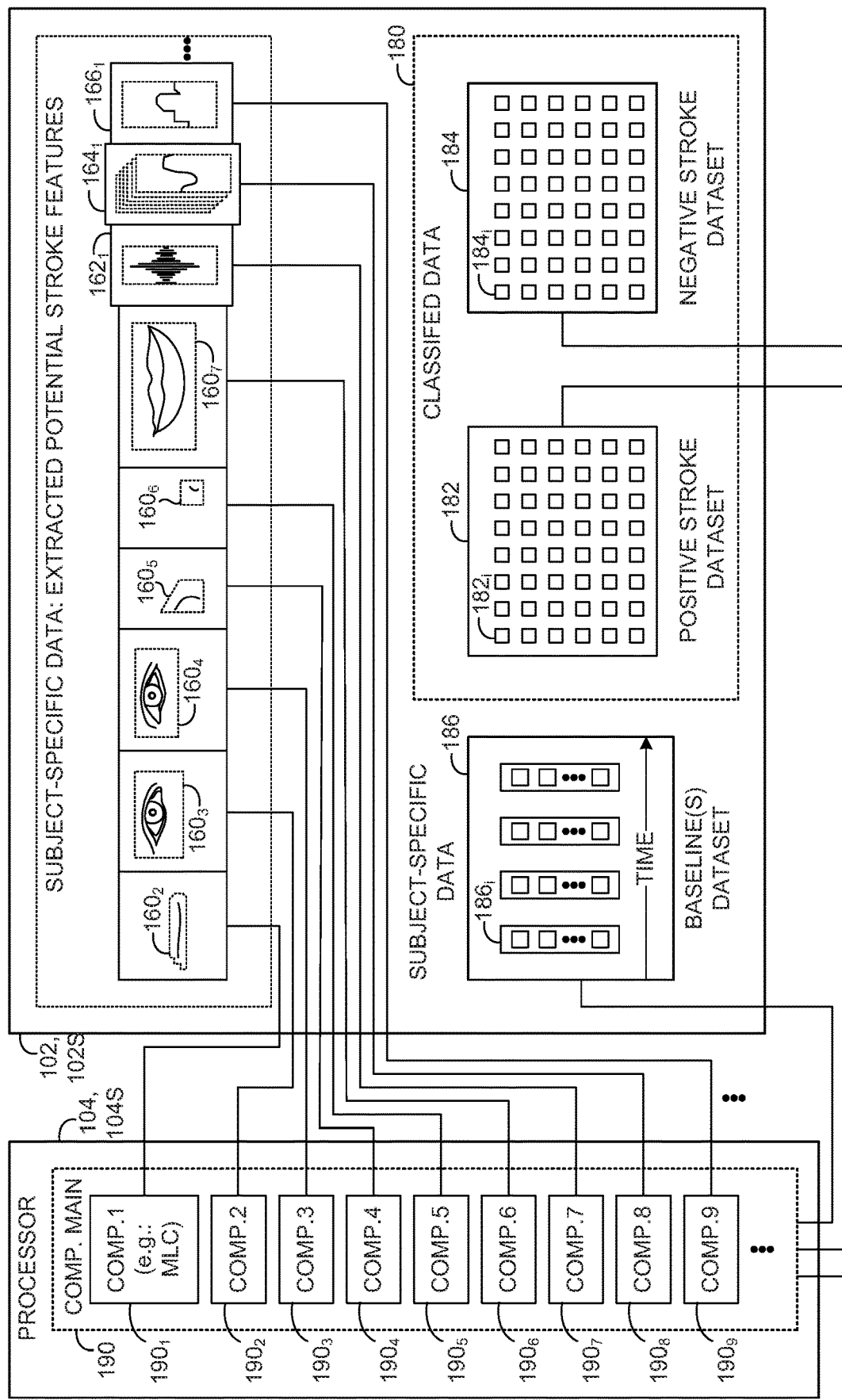
FIG. 5 is a schematic diagram illustrating comparison between extracted potential stroke features and classified data in a database, constructed and operative according to the disclosed technique.

Following the extraction of the potential stroke features from the clinical measurement data, the extracted potential stroke features are then compared with classified sampled data in a patient database (interchangeably denoted herein as "database") acquired from a plurality of subjects, each positively diagnosed with at least one stroke condition. To further detail this step of the disclosed technique, reference is now made to FIG. 5, which is a schematic diagram illustrating comparison between extracted potential stroke features and classified data in a database, constructed and operative according to the disclosed technique. FIG. 5 illustrates an exemplary implementation of internal elements (blocks) within server database 102S (likewise applicable to database 102) and server processor 104S (likewise applicable to processor 104) that are involved in the comparing step of the disclosed technique. Specifically, server database 102S includes a classified data section 180 that includes a positive stroke dataset 182, and a negative stroke dataset 184. Server database 102S further includes subject-specific data stored therein that includes subject-specific extracted potential stroke features $160_2$, $160_3$, $160_4$, $160_5$, $160_6$, $160_7$, $162_1$, $164_1$, $166_1$, as well as a subject-specific baseline(s) dataset 186. The subject specific data is part of the user (subject's) account stored in server database 102S of server 101S. Alternatively, all or at least part of the subject-specific data is stored in a memory storage (i.e., at least one of the hardware device, in software, firmware, removable storage medium, etc.) of client device $101C_1$ associated with the subject (e.g., an owner, a user, of the client device). For example, baseline(s) dataset 186 is stored in memory storage of the client device (i.e., "in-memory database") and the extracted potential stroke features are stored on server database 102S. Other combinations of distributing the subject-specific data among various data storage entities (e.g., as in a distributed database) that may include server database 102S, client devices 101, as well as external cloud database(s), are also viable options according to the disclosed technique.

Baseline(s) dataset 186 includes at least one entry $186_i$ that is a time-dependent baseline profile of subject 10 (where i denotes a general index of the i-th entry in baseline dataset 186 at a particular point in time). There may typically be a plurality of baseline entries for subject 10 that are time-wise ordered, as shown in FIG. 5. Positive stroke dataset 182 includes a plurality of entries $182_i$, (where i denotes a general index of an i-th entry), where each entry $182_i$ is sampled data associated with an individual positively diagnosed (and verified) with at least one stroke condition. Each entry $182_i$ constitutes as labeled sampled data (interchangeably denoted herein "labeled sampled data entry", and "labeled sampled data item"). Each entry $182_i$ in positive stroke dataset 182 acquired from an individual positively diagnosed with a stroke condition includes at least two fields: stroke type (i.e., ischemic, and hemorrhagic), and its corresponding brain location (generic)). There may be only one entry sampled from a particular individual in a population, or a plurality of entries sampled from the same individual. Each entry $182_i$ includes at least one quantified extracted feature that is associated with a probability threshold that may be indicative to at least one stroke condition. For example, an individual positively diagnosed with a stroke condition may experience partial facial paralysis that manifests as one-sided facial drooping of particular facial landmarks. An entry in positive stroke dataset 182 corresponding to that example can be represented by a multi-dimensional matrix or vectors representing individual facial landmarks points (coordinates), the direction and magnitude of change with respect to corresponding features on the other side of the face (e.g., drooping of one eye with respect to another). Note that extracted potential stroke features can possess attributes that may indicate, for example facial paralysis, which in itself may not necessarily be conclusive to the presence of a stroke condition, as there may be other causes such as Bell's palsy, and Lyme disease that exhibit similar clinical features. The disclosed technique therefore relies on extracting a plurality of potential stroke features so as to enable differential diagnosis of a stroke condition from various other unrelated diseases, symptoms, and conditions, as well as for the purpose of enhancing the estimation to the probability of a stroke condition. This enables differential diagnosis of stroke mimics that are generally non-vascular conditions that simulate acute ischemic stroke (e.g., seizures, psychiatric disorders, etc.) but are not a stroke. Another example of an entry in positive stroke dataset 182 includes a particular parametric representation of a voice data model that is characteristic to slurred speech of an individual positively diagnosed with at least one stroke condition. The individual entries $182_i$ in positive stroke dataset 182 are labeled sampled data that are classified according to various criteria type (e.g., image data, sound data), quantitative measures, and the like.

Negative stroke dataset 184 includes a plurality of entries 184i where each entry 184i includes data sampled from an individual negatively diagnosed for a stroke condition (i.e., are verified not to have a stroke condition ("ground truth")). Likewise, there may be only one entry sampled from a particular individual in a population, or a plurality of entries sampled from the same individual.

Processor 104S includes a main comparator block 190, which in turn may include a plurality of individual comparators $190_1$, $190_2$, $190_3$, $190_4$, $190_5$, $190_6$, $190_7$, $190_8$, $190_9$ (collectively denoted herein as "comparators $190_1$-$190_9$"). Main comparator block 190 may be implemented in at least one of hardware, software, firmware, and a combination thereof. Main comparator block 190 is configured and operative to compare subject-specific extracted potential stroke features $160_{1-7}$, $162_1$, $164_1$, and, $166_1$ with classified sampled data in positive stroke dataset 182. Specifically, comparator $190_1$ compares extracted potential stroke feature $160_2$ with positive stroke dataset 182 so as to produce a result that represents a quantitative measure that indicates how extracted potential stroke feature $160_2$ matches with corresponding entries 182i of the same type (i.e., image data). Similarly, comparators $190_2$-$190_9$ respectively compare extracted potential stroke features $160_{3-7}$, $162_1$, $164_1$, and $166_1$ with positive stroke dataset 182, so as to produce respective outputs that represent quantitative measures that indicate how these extracted potential stroke features match with corresponding entries 182i of their same type. An output of the comparison is a quantitative measure to how a particular extracted potential stroke feature matches either one of positive stroke dataset 182, negative stroke dataset 184, or both (i.e., an indeterminate result, e.g., in case there's a 50% match to positive stroke dataset 182 and 50% match to negative stroke dataset 184). In addition (and optionally), comparators $190_1$-$190_9$ are configured and operative to compare extracted potential stroke features $160_1$-$160_7$, $162_1$, $164_1$, and $166_1$ with negative stroke dataset 184, so as to produce respective outputs that represent quantitative measures indicating how these extracted potential stroke features match with corresponding entries $184_i$ of their same type. Generally, the use of both positive stroke dataset 182 and negative stroke dataset 184 in the comparison enhances the estimation of the likelihood in determining the presence of a stroke condition of the subject.

Alternatively, there is one comparator associated for each modality type (e.g., image data, sound data, etc.) (not shown). According to this alternative configuration, one comparator is used to compare extracted potential stroke features $160_1$, $160_2$, $160_3$, $160_4$, $160_5$, $160_6$, and $160_7$ (image data) with classified data in positive stroke dataset 182, and optionally with negative stroke dataset 184. Similarly, there are separate and distinct comparators, respectively employed to compare extracted potential stroke feature $162_1$ (sound data), extracted potential stroke feature $164_1$ (movement data), as well as extracted potential stroke feature $166_1$ (tactile data) with classified data in positive stroke dataset 182, and optionally with negative stroke dataset 184. Further alternatively, there is one comparator that is configured and operative to perform all the required comparisons.

According to a particular configuration, main comparator block 190 is implemented as a machine learning classifier (denoted herein "MLC") that is configured and operative to employ both positive stroke dataset 182 as well as negative stroke dataset 184, both of which constitute as training data in which the MLC bases and produces an output that corresponds to an input of an extracted potential stroke feature. Generally, the input to the MLC is an extracted (and preprocessed) potential stroke feature, and the corresponding output of the MLC is a quantitative measure to how the inputted extracted potential stroke feature fits to the trained data, the latter of which can be represented by a mathematical model, as will be further detailed hereinbelow. In one implementation, there is a plurality of different MLCs (i.e., equal to the number of comparators $190_1$-$190_9$) for each subject-specific extracted potential stroke feature. According to another implementation, there is one MLC for each modality type (e.g., image data, sound data, etc.) (not shown). According to a further implementation, there is one MLC (e.g., main comparator 190 is implemented by one MLC). Typical examples of MLCs include artificial neural networks (ANNs), decision trees, support vector machines (SVMs), Bayesian networks, k-nearest neighbor (KNN) classifiers, regression analysis (e.g., linear, logistic), etc.

Figure 6:
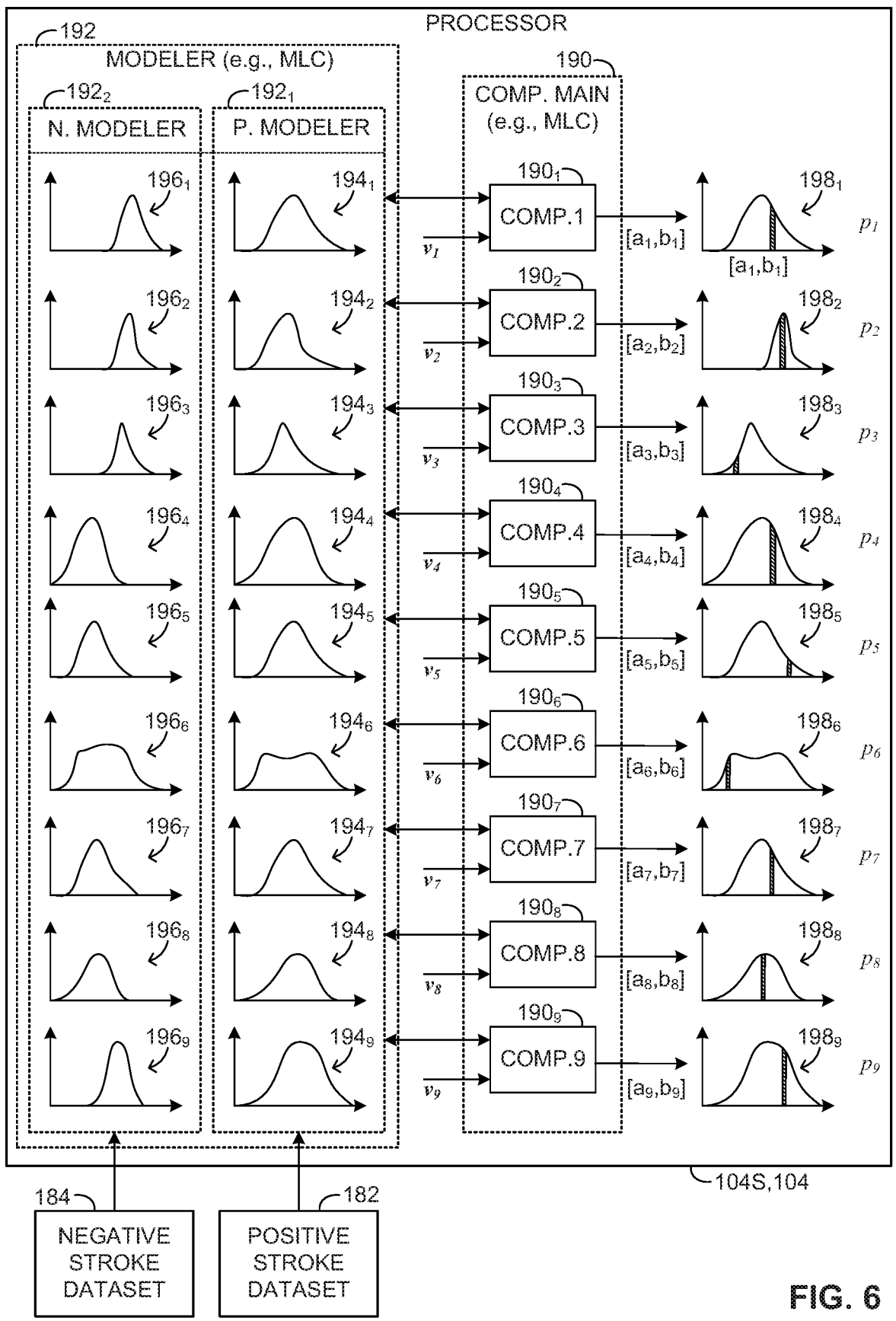
FIG. 6 is a schematic diagram partly showing procedures involved in producing an estimation to the likelihood of a stroke condition, according to the principles of the disclosed technique.

To further explicate the particulars of the disclosed technique, reference is now further made to FIG. 6, which is a schematic diagram partly showing procedures involved in producing an estimation to the likelihood of a stroke condition, according to the principles of the disclosed technique. FIG. 6 shows processor 104S (or 104) that includes main comparator block 190 having a plurality of discrete comparators $190_1$-$190_9$ (e.g., implemented by MLCs), as well as a modeler 192. Modeler 192 may be subdivided into a positive stroke modeler $192_1$ sub-block and a negative stroke modeler $192_2$ sub-block. Modeler 192 is generally implemented in at least one of hardware, software, firmware, and a combination thereof. Modeler 192 is generally configured and operative to construct mathematical models from the positive stroke dataset 182 as well as from negative stroke dataset 184. Specifically, positive stroke modeler $192_1$ sub-block is configured and operative to construct mathematical models $194_1$, $194_2$, $194_3$, $194_4$, $194_5$, $194_6$, $194_7$, $194_8$, and $194_9$ from positive stroke dataset 182. Analogously, negative stroke modeler $192_2$ sub-block is configured an operative to construct mathematical models $196_1$, $196_2$, $196_3$, $196_4$, $196_5$, $196_6$, $196_7$, $196_8$, and $196_9$ from negative stroke dataset 184. The mathematical model may be, for example represented by a probability distribution function (also denoted interchangeably herein as "probability density function", and "PDF" for short) that is basically a function having at least one input and whose possible output values are probabilities of occurrence of different results/outcomes of an experiment (i.e., different outcomes and their associated probabilities). There are various types of PDFs (e.g., Gaussian distribution function, Gamma distribution function, etc.) each of which is defined by its respective parameters (e.g., mean ($\mu$), variance ($\sigma^2$), and the like). Modeler 192 is configured and operative to construct the individual models $194_1$-$194_9$ and $196_1$-$196_9$ which includes determining the parameters for each model (not shown). The disclosed technique may continuously update ("learn") each model via its defining parameters by using training data (in database 102) through a process of parameter estimation and optimization, such that the best values for these parameters are determined e.g., via maximum-likelihood techniques.

Each comparator (also herein MLC) $190_1$-$190_9$ is configured and operative to receive as input the extracted and preprocessed potential stroke features (as detailed in conjunction with FIG. 5), which may be termed herein as a "feature vectors", denoted respectively as $v_1$, $v_2$, $v_3$, $v_4$, $v_5$, $v_6$, $v_7$, $v_8$, and $v_9$ in FIG. 6. Each MLC or comparator is then configured and operative to assess how each respective input feature vector compares with positive stroke dataset 182 and negative stroke dataset 184, and then further configured to output a result that optimally matches a sample space in data sets 182 and 184. The comparison result the can be represented as an interval in the sample space of positive stroke dataset 182 and/or as an interval in the sample space of negative stroke dataset 184. Processor 104S is then configured to compute a respective probability by integrating the PDF over that interval as denoted by $198_1$, $198_2$, $198_3$, $194_4$, $198_5$, $198_6$, $198_7$, $198_8$, and $198_9$ in FIG. 6. Particularly, comparator $190_1$ compares feature vector $v_1$ with positive stroke dataset 182 (the plurality of entries $182_i$ thereof) as well as negative stroke dataset 184 (the plurality of entries $182_i$ thereof) and determines an optimal match of this comparison by outputting at least one interval $[a_1, a_2]$ in the sample space (i.e., in datasets 182 and 184), where the optimal match occurs (i.e., in positive stroke dataset 182 or negative stroke dataset 184). In this particular example the optimal match occurs in positive stroke dataset 182, the corresponding model of which is PDF $194_1$. Processor 104S integrates PDF $194_1$ over the determined interval $[a_1, b_1]$, represented by $198_1$, thereby yielding a probability $p_1$. Note that in this example, the interval is one-dimensional, however, the sample space is typically multi-dimensional and so is the integration of several variables (e.g., a multiple integral, and multivariate probability distribution). Analogously, comparator $190_2$ compares feature vector $v_2$ with positive stroke dataset 182 (the plurality of entries $182_i$ thereof) as well as negative stroke dataset 184 (the plurality of entries $182_i$ thereof) and determines an optimal match of this comparison thereby outputting at least one interval $[a_2, b_2]$ in the sample space where the optimal match occurs. In this particular example the optimal match occurs in negative stroke dataset 184, the corresponding model is PDF $196_2$. Processor 104S integrates PDF $196_2$ over the determined interval $[a_2, b_2]$, represented by $198_2$ thereby yielding a probability $p_2$. Analogously, processor 104S performs this process for $v_3$, $v_4$, $v_5$, $v_6$, $v_7$, $v_8$, and $v_9$ thereby yielding respective probabilities $p_3$, $p_4$, $p_5$, $p_6$, $p_7$, $p_8$, and $p_9$. Although the above description is with respect to PDFs is for continuous random variables, the disclosed technique is likewise applicable to probability mass functions (PMFs) of discrete random variables. Without loss of generality, the PDF approach is an example implementation of the disclosed technique.

Figure 7:
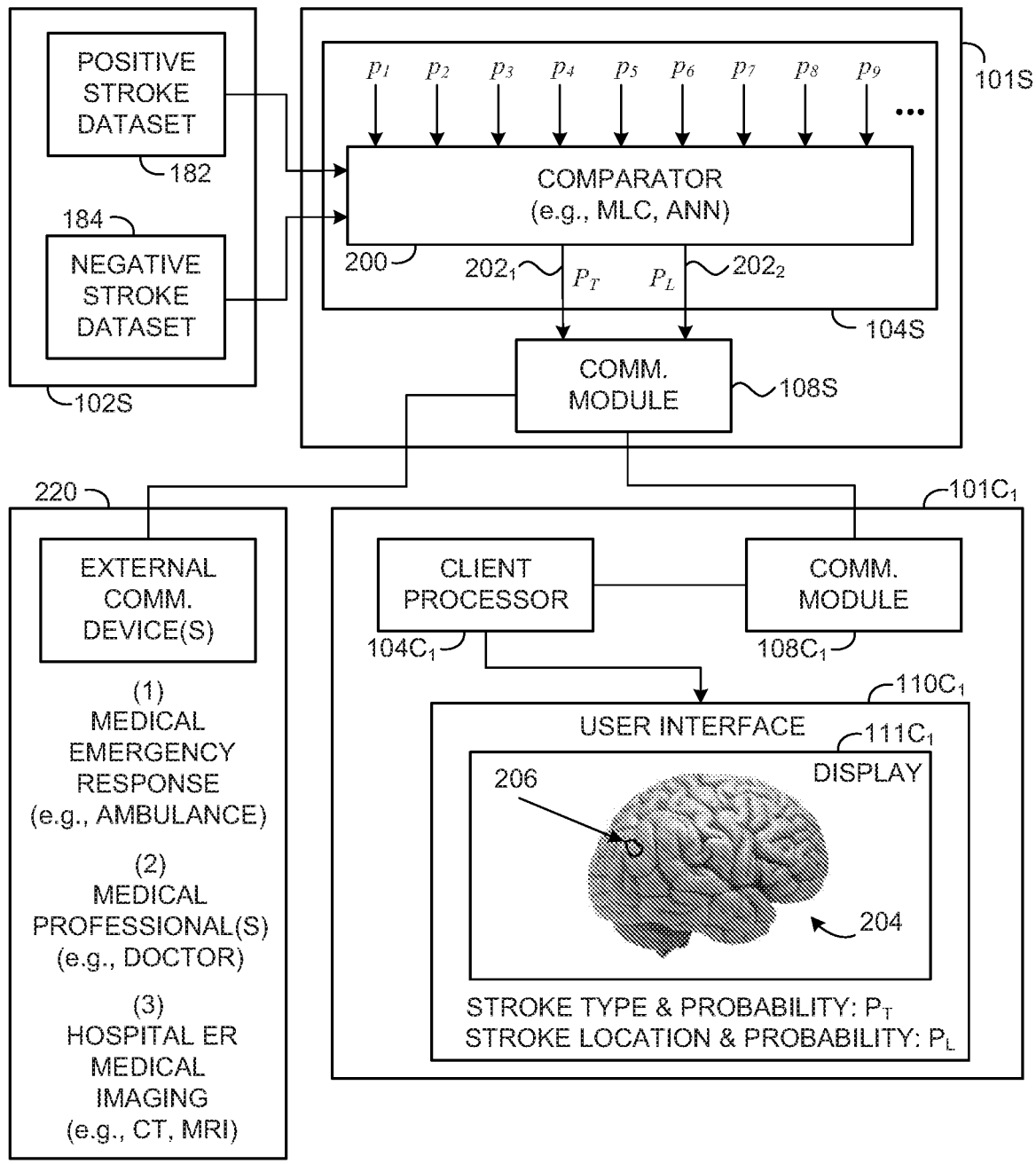
FIG. 7 is a schematic diagram further showing procedures involved in producing an estimation to the likelihood of a stroke condition, according to the principles of the disclosed technique.

In determining a probability for a type of a stroke condition, and a probability of a corresponding stroke location, processor 104S is configured and operative to use the results of the comparisons between the potential stroke features and the classified sampled data in the positive stroke dataset (as well as optionally with the negative stroke dataset). To further detail the particulars of this aspect of the disclosed technique, reference is further made to FIG. 7, which is a schematic diagram further showing procedures involved in producing an estimation to the likelihood of a stroke condition, according to the principles of the disclosed technique. FIG. 7 shows server processor 104S further including a comparator 200 that may be implemented for example by a MLC, an ANN, and the like. Comparator 200 receives probabilities $p_1$, $p_2$, $p_3$, $p_4$, $p_5$, $p_6$, $p_7$, $p_8$, and $p_9$ and is configured and operative to determine probabilities $P_T$ and $P_L$ as outputs $202_1$ and $202_2$, respectively by use of database 102S. As aforementioned, each entry $182_i$ in positive stroke dataset 182 that has been acquired from an individual positively diagnosed with a stroke condition includes at least two fields: (1) stroke type; and (2) its corresponding brain location. According to one standard implementation of comparator 200, the collective as well as individual contributions of the probabilities $p_1$-$p_9$ are weighted so as to find an optimal match with respect to sampled data entries in database 102S. According to another implementation, comparator 200 is an MLC (e.g., ANN) that is pre-trained (e.g., via an MLC) to yield a result that optimally fits with labeled sampled data in database 102. Comparator 200 yields an output $202_1$ as a probability $P_T$ for a type of stroke condition of subject 10, and an output $202_2$ as a probability $P_L$ for a corresponding location of a stroke condition with respect to a brain location of subject 10. The determined probability of a stroke condition at a particular brain location may be described in terms of a generic brain location, as various brain locations, areas, or regions are associated with different brain functions (e.g., motor and speech production, voluntary eye movement, vision, language comprehension, equilibrium and muscle coordination, etc.). For example, a stroke in the posterior cerebral artery (PCA) may typically affect vision; while cerebellar strokes may typically affect balance and coordination, etc. Processor 101S conveys outputs $202_1$ and $202_2$ to communication module 108, which in turn is configured and operative to communicate (e.g., transmit) these outputs through signals encoding data pertaining to $P_T$ and $P_L$ to communication module $108C_1$ of client device $101C_1$. Communication module $108C_1$ receives the data encoded signals and provides them to client processor $104_1$, which in turn is configured and operative to direct user interface $110C_1$ to present the $P_T$ and $P_L$ data via at least one sensory modality, e.g., visually via a display $111C_1$, audibly (not shown), etc. Display $111C_1$ is configured and operative to display the determined stroke type and its probability $P_T$ as well as a corresponding stroke location and its respective probability $P_L$, as well as a graphical representation of a brain model that includes a superimposed highlighted region 206 that corresponds to the determined stroke location. Furthermore, systems $101_1$ and $101_2$ of the disclosed technique may use baseline dataset 186 for augmenting the estimated probabilities $P_T$ and $P_L$ by using its corresponding data to minimize false positive classifications, as well as false negative classifications. Baseline dataset 186 is, according to a particular implementation, inputted to main comparator 190 (FIG. 5) so as to take into account time-dependent baseline entries $186_i$ in the comparison (this also applies to the MLC implementation of the disclosed technique). In case baseline dataset 186 includes baseline subject-specific entries $186_i$ acquired at different times, systems $100_1$ and $100_2$ are configured and operative to compare between them and to use their deltas (i.e., differences) for the purpose of augmenting at least one of: (1) the comparison (i.e., between potential stroke features and classified sampled data), and (2) the determination of a probability of stroke type and a probability of corresponding stroke location.

In addition, communication module 108S is configured and operative to communicate outputs $202_1$ and $202_2$ through signals encoding data pertaining to $P_T$ and $P_L$ to external communication devices 220 (also denoted herein interchangeably as mobile or immobile "patient management console units", "management console units", and "management console") of various entities such as: (1) a medical emergency response service (e.g., operating an ambulance service); (2) medical professional(s) (e.g., a doctor specialized in treating strokes, a personal doctor of subject 10, paramedics, etc.); (3) a hospital emergency room (ER) including a neuroimaging department (e.g., employing computerized tomography (CT), magnetic resonance imaging (MRI) in general and functional-MRI (fMRI) in particular, positron-emission tomography (PET), and the like); (4) subject's 10 relatives (e.g., family member(s)); (5) an operator of systems $101_1$ and $101_2$ of the disclosed technique; and the like. Probabilities $P_T$ and $P_L$ transmitted to external communication devices 220 also include information about subject 10 that can include name, identification number, age, current location, etc. The system and method of the disclosed technique are configured and operative to present (e.g., provide, display) at least one ROI, and POI in the extracted clinical measurement data that corresponds with a highest estimated likelihood of the stroke condition, according to the determined probabilities $P_T$ and $P_L$ so as to reduce time for treatment by medical staff, physician, etc.

Reference is now made to FIG. 8, which is a schematic diagram of a method, generally referenced 250, for estimating a likelihood of a stroke condition of a subject, constructed and operative in accordance with the disclosed technique. Method 250 includes a plurality of procedures (steps), which initiates with procedure 252. In procedure 252, clinical measurement data pertaining to a subject is acquired. The clinical measurement data includes at least one of image data, sound data, movement data, and tactile data. With reference to FIGS. 1A, 1B, and 2, acquisition unit 106 of system $100_1$ (FIG. 1A) and acquisition units $106C_1$, $106C_2$, . . . , $106C_N$ of respective client devices $101C_1$, $101C_2$, . . . , $101_N$ of system $100_2$ (FIG. 1B) include at least one of image sensor $120C_1$ (FIG. 2, exemplary shown for client device $101C_1$), sound sensor $122C_1$, movement sensor $124C_1$, and tactile sensor $126C_1$ that are each configured respectively to acquire image data 130, sound data 134, movement data 138, and tactile data 142 pertaining to subject 10.

In procedure 254, from the clinical measurement data, potential stroke features are extracted according to at least one predetermined stroke assessment criterion. With reference to FIGS. 1A, 1B, 3 4, and Tables 1-12 potential stroke features are extracted, via processors 104 (FIG. 1A) and 104S (FIG. 1B) as follows. Spatial ROIs $160_2$, $160_3$, $160_4$, $160_5$, $160_6$, and $160_7$ from a time POI, i.e., image $130_4$ are extracted from image data 130. ROI $162_1$ is extracted from sound data 134. Multi-dimensional ROI $164_1$ is extracted from movement data 138. ROI $166_1$ is extracted from tactile data 142. The potential stroke features are extracted according to at least one predetermined stroke assessment criterion in Tables 1-12.

In procedure 256, the potential stroke features are compared with classified sampled data acquired from a plurality of subjects, each positively diagnosed with at least one stroke condition, defining a positive stroke dataset. With reference to FIGS. 1B and 5, main comparator 190 (e.g., MLC) (FIG. 5) which may include a plurality of comparators $190_1$-$190_9$ compares (extracted) potential stroke features $160_2$-$160_7$, $162_1$, $164_1$, and $166_1$ with classified data section of database 180 (FIG. 5) of server database 102S (FIG. 1B) acquired from a plurality of subjects, each positively diagnosed with at least one stroke condition. The classified data pertaining to the plurality of subjects positively diagnosed with at least one stroke condition is part of positive stroke dataset 182. Optionally additionally, the potential stroke features are compared with classified sampled data in a patient database acquired from a plurality of subjects, each negatively diagnosed with a stroke condition. The classified data pertaining to the plurality of subjects negatively diagnosed with a stroke condition is part of negative stroke dataset 184 (FIG. 5).

In procedure 258, a probability of a type of stroke condition, and a probability of a corresponding stroke location of the stroke condition with respect to a brain location of the subject are determined according to the comparing procedure. With reference with FIGS. 6 and 7, modeler (block) 192 (of processor 104S) (FIG. 6) constructs models from positive stroke dataset 182 as well as optionally from negative stroke dataset 184. Main comparator (block) 190 (of processor 104S) assesses (e.g., by comparison) how each respective input feature vector compares with positive stroke dataset 182 and negative stroke dataset 184, and then outputs a result that optimally matches a sample space in data sets 182 and 184. Processor 104S computes respective probabilities $p_1$, $p_2$, $p_3$, $p_4$, $p_5$, $p_6$, $p_7$, $p_8$, and $p_9$ according to the results of main comparator block 190. Comparator (block)

200 (FIG. 7) of processor 104S receives probabilities $p_1$, $p_2$, $p_3$, $p_4$, $p_5$, $p_6$, $p_7$, $p_8$, and $p_9$ and determines probability $P_T$ (i.e., for a type of stroke condition of subject 10), and a probability $P_L$ (i.e., for a corresponding location of the stroke condition with respect to a brain location of subject 10).

Figure 9C:
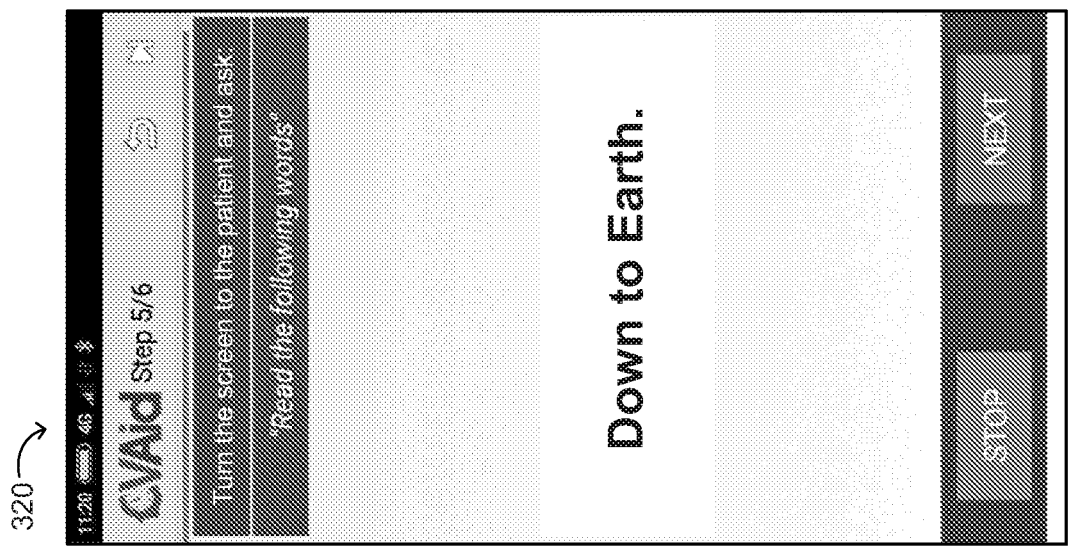
FIG. 9C is an exemplary screenshot of a language subtest of an example NIHSS test performed by the system of the disclosed technique.
Figure 9B:
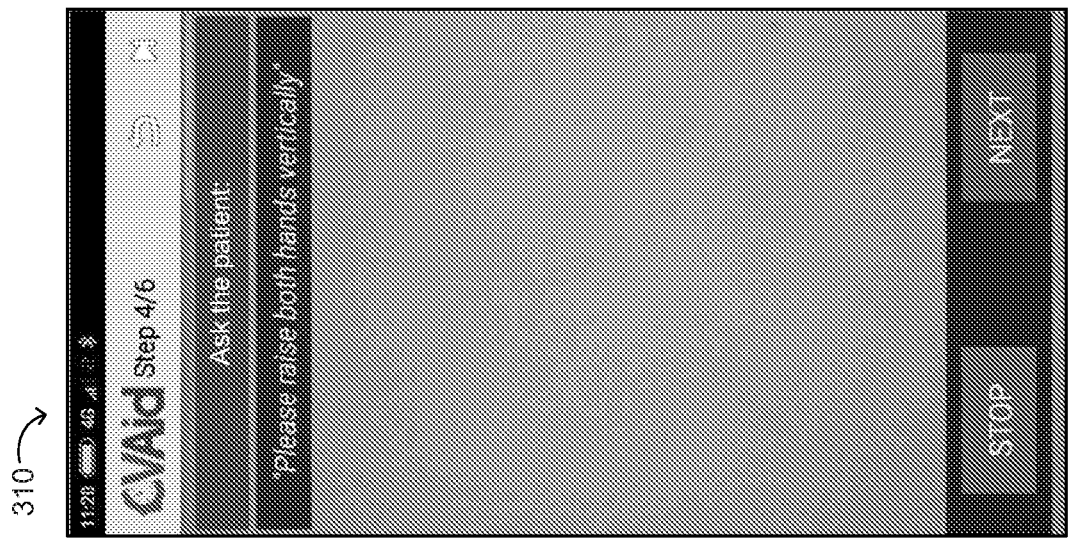
FIG. 9B is an exemplary screenshot of a motor arm subtest in an example NIHSS test performed by the system of the disclosed technique.
Figure 9A:
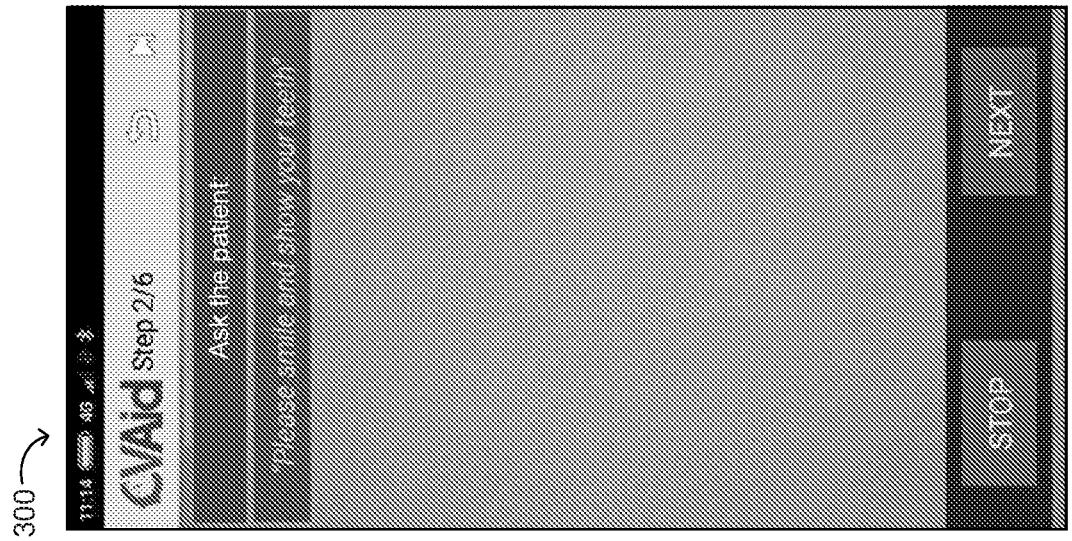
FIG. 9A is an exemplary screenshot of a facial palsy subtest in an example NIHSS test performed by the system of the disclosed technique.

A real-world example implementation of the disclosed technique now follows. Reference is now made to FIGS. 9A, 9B, and 9C. FIG. 9A is an exemplary screenshot, generally referenced 300, of a facial palsy subtest in an example NIHSS test performed by the system of the disclosed technique. FIG. 9B is an exemplary screenshot, generally referenced 310, of a motor arm subtest of an example NIHSS test performed by the system of the disclosed technique. FIG. 9C is an exemplary screenshot, generally referenced 320, of a language subtest of an example NIHSS test performed by the system of the disclosed technique. Screenshot 300 (also denoted herein interchangeably as "screen capture") in FIG. 9A shows a user interaction prompt of system 100₂ for subject 10 using (directly or indirectly) client device (e.g., 101C₁) that instructs subject 10 via user interface 110C₁ (FIG. 1B) (e.g., screen) to smile and show teeth: "Please smile and show your teeth". Acquisition unit 106C₁ of client device 101C₁ captures clinical measurement data (e.g., video data that includes image data 130 and sound data 134) pertaining to subject 10. Screenshot 310 in FIG. 9B shows a user interaction prompt of system 100₂ via client device 101C₁ instructing subject 10 to raise both hands vertically: "Please raise both hands vertically" (e.g., for 10 seconds). Acquisition unit 106C₁ of client device 101C₁ captures clinical measurement data pertaining to subject 10 during this subtest. Screenshot 320 in FIG. 9C shows a user interaction prompt of system 100₂ via client device 101C₁ instructing subject 10 to read several words displayed (e.g., appearing on a screen of user interface 110C₁): "Down to Earth." Acquisition unit 106C₁ of client device 101C₁ captures clinical measurement data pertaining to subject 10 during this subtest.

Figure 10:
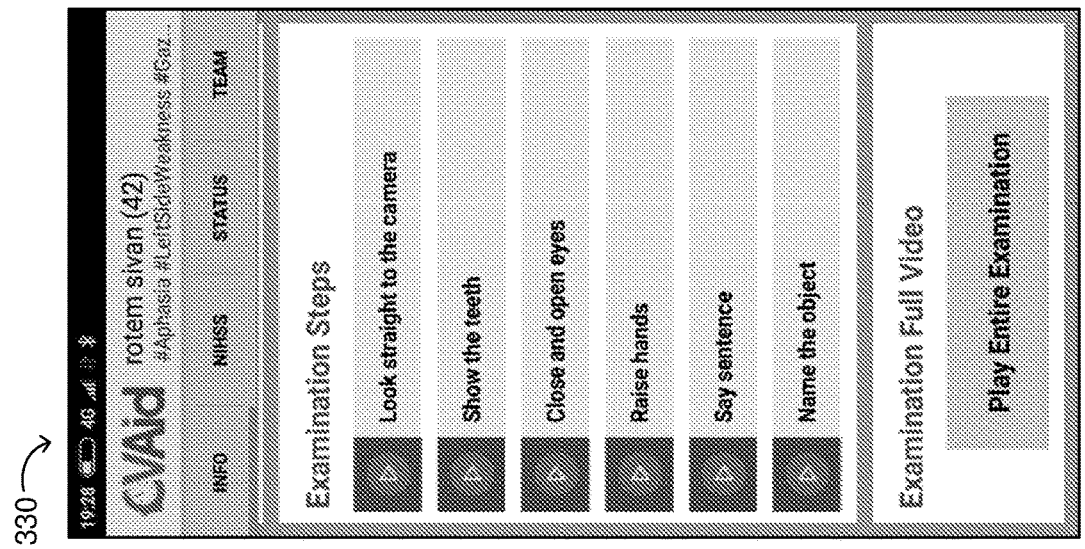
FIG. 10 is an exemplary screenshot showing acquired clinical measurement data pertaining to the subject that is provided remotely to a physician via at least one external communication device.

Reference is now further made to FIG. 10, which is an exemplary screenshot, generally referenced 330, showing acquired clinical measurement data pertaining to the subject that is provided remotely to a physician via at least one external communication device. FIG. 10 shows an example of clinical measurement data in the form of video files (i.e., video examination) acquired from subject during a user interaction prompt of system 100₂ for each different subtest in the example NIHSS test. Systems 100₁ and 100₂ enables a physician to remotely view clinical measurement data shown in FIG. 10 via external communication device 220 embodied as and interchangeably denoted as a mobile patient management console unit that is installed with software and/or firmware that facilitates review and analysis of the acquired clinical measurement data.

Figure 11:
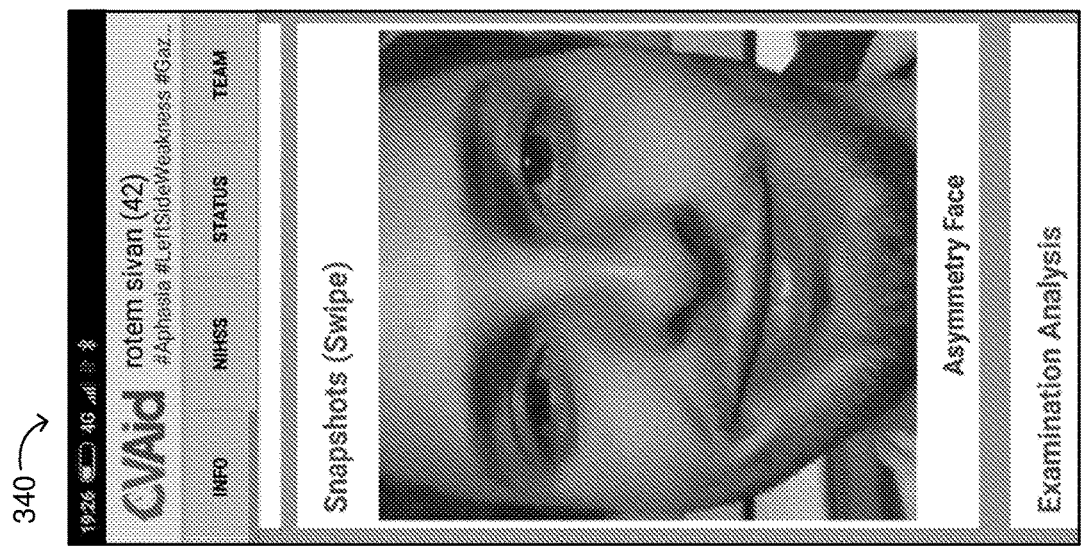
FIG. 11 is an exemplary screenshot showing an example of a spatial region of interest (ROI) from a temporal point of interest (POI) in image data (video), identified as being a potential stroke feature.

Reference is now further made to FIG. 11, which is an exemplary screenshot, generally referenced 340, showing an example of a spatial region of interest (ROI) from a temporal point of interest (POI) in image data (video), identified as being a potential stroke feature. FIG. 11 shows an example of processor 104S identifying a potential stroke feature (i.e., an asymmetric smile), a spatial ROI in a particular frame (temporal POI) in video data (image data 130 and sound data 134. The mobile patient management console 220 enables the physician (e.g., located remotely from subject 10, such as at a hospital, clinic, etc.) to view only the relevant ROIs and POIs (i.e., and not the entire clinical measurement data, such as the entire video), thereby saving time in the treatment of a stroke event. Furthermore the systems of the disclosed technique may employ medical data compartmentalization techniques so that each physician in a medical team may have his/her own patient management console that is customized for his/her specific role and authority in the stroke diagnosis and treatment process (e.g., a list of commands, functions, and medical data (e.g. raw data, medical reports, etc.) may only be available or viable to those users authorized to view and make use of them).

Figure 12:
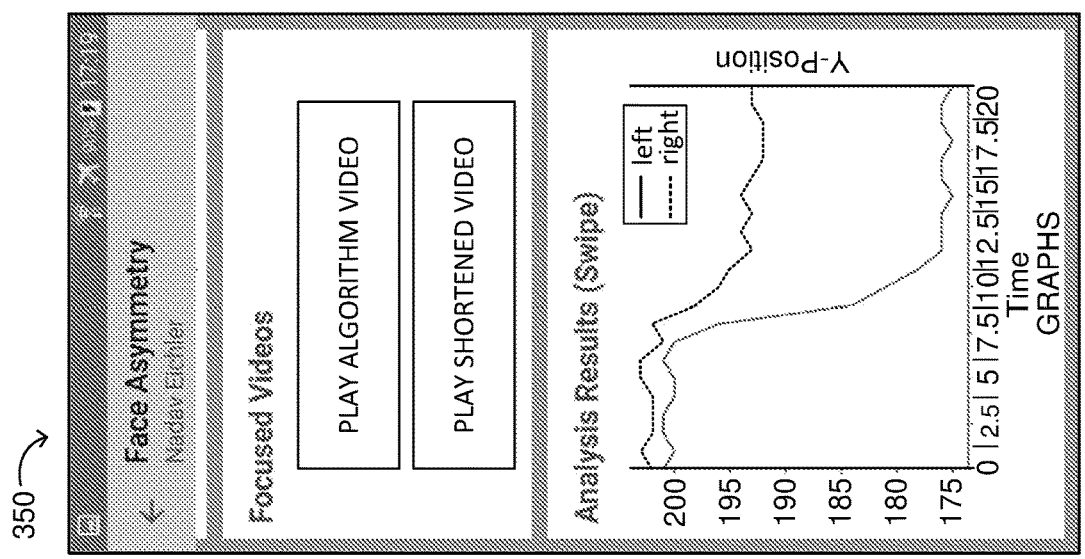
FIG. 12 is an exemplary screenshot, showing an example of image analysis of facial bilateral symmetry as a function of time for the case shown in FIG. 11 (asymmetric smile)

Reference is now further made to FIG. 12, which is an exemplary screenshot, generally referenced 350, showing an example of image analysis of facial bilateral symmetry as a function of time for the case shown in FIG. 11 (asymmetric smile). Specifically, processor 104S is configured and operative to analyze the progress (i.e., change) of potential stroke features as a function of time, and to present the analysis to a physician (particularly, the most informative image frame(s)). FIG. 12 shows a graph of an amalgamated position of right facial landmarks as well as a graph of an amalgamated position of left facial landmarks that are related to smiling of a subject of FIG. 11, and their interrelationship.

Figure 13:
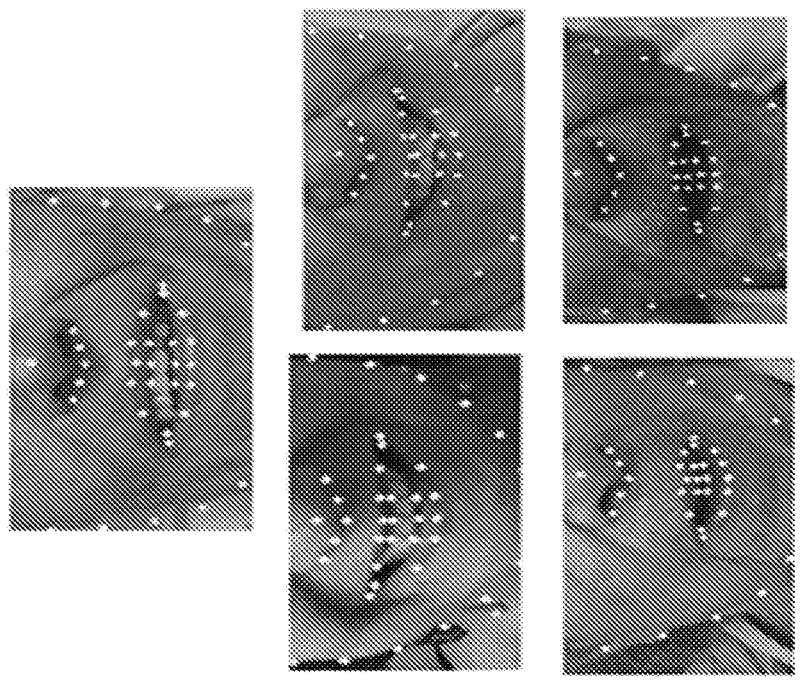
FIG. 13 is a collection of images acquired from several subjects, showing their lower faces superimposed with a plurality of image markers for algorithmically tracking facial landmarks, according to the disclosed technique.

Reference is now further made to FIG. 13, which is a collection of images acquired from several subjects, generally referenced 360, showing their lower faces superimposed with a plurality of image markers for algorithmically tracking facial landmarks, according to the disclosed technique. Specifically, FIG. 13 shows five different images of five peoples' lower faces, whose facial landmarks are superimposed by image markers (objects). Processor 104S is configured and operative to operate a program (e.g., an algorithm) that analyzes image data 130 as well as and sound data 134 typically in the form of video for each subject, such that facial landmarks (e.g., lips, face contour nose, etc.) in individual image frames from the video are identified and tracked in time so as to identify potential stroke features such as smile asymmetry, speech irregularities such as irregular connection between word pronunciation and lip movements (e.g., checked with respect to subject's baseline profile), and the like. Processor 104S is configured to derive mathematical relationships between the individually tracked image markers (and sound markers—not shown) from the clinical measurement data (in this example, video) such as speed, acceleration of the image markers between image frames, open/close time of lips, facial asymmetry characteristics, etc.

Figure 14:
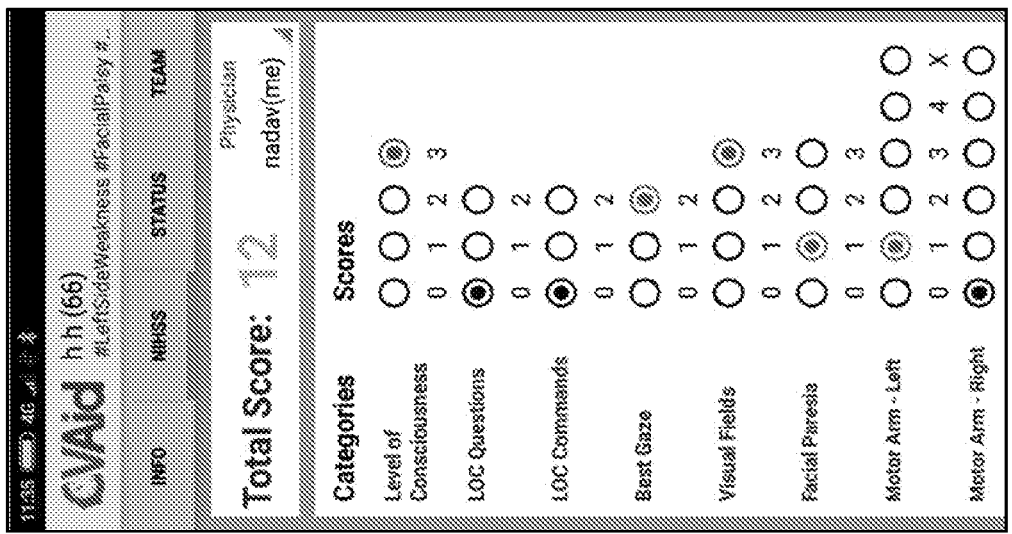
FIG. 14 is an exemplary screenshot showing an example of individual scores for various subtests in an example NIHSS test as yielded by the systems of the disclosed technique.

Reference is now further made to FIG. 14, which is an exemplary screenshot, generally referenced 370, showing an example of individual scores for various subtests in an example NIHSS test as yielded by the systems of the disclosed technique. Specifically, screenshot 370 shows different categories and subtests in an example NIHSS test performed on subject 10 and its corresponding scores. Processor 104S is configured and operative to calculate a score based on extracted clinical measurement data, according to at least one predetermined stroke assessment criterion, which in this case are a plurality of criteria that are part of the NIHSS test (see Tables 1-12). The mobile management consoles 220 are configured and operative to display the individual scores, as well as enable a physician to observe the scores, approve the scores, remark on individual scores, modify the scores (e.g., digitally fill, change, update the individual medical score rubrics, as well as receive automatic suggestions from the system for each one of the individual medical scale categories).

Figure 15:
FIG. 15 is an exemplary screenshot showing an example of timing information relating to the onset of a detected a stroke condition of a subject and personal information relating thereto.

Reference is now further made to FIG. 15, which is an exemplary screenshot, generally referenced 380, showing an example of timing information relating to the onset of a detected a stroke condition of a subject and personal information relating thereto. Processor 104S calculates and continuously tracks a detected and ongoing stroke condition in real-time (i.e., real-time diagnosis), as well as operative to facilitate presentation (i.e., directs the display of) the timing information via the management consoles 220. The timing information may be presented as a continuously real-time updated time (e.g., a clock) from the onset of detected symptoms, a continuously real-time updated time (e.g., a clock) from a detected stroke condition by the system of the disclosed technique, and the like. Patient's/subject's personal information may include subject's name, age, symptoms reported by a paramedic in an ambulance, in subject's location (e.g., home, etc.).

Figure 16:
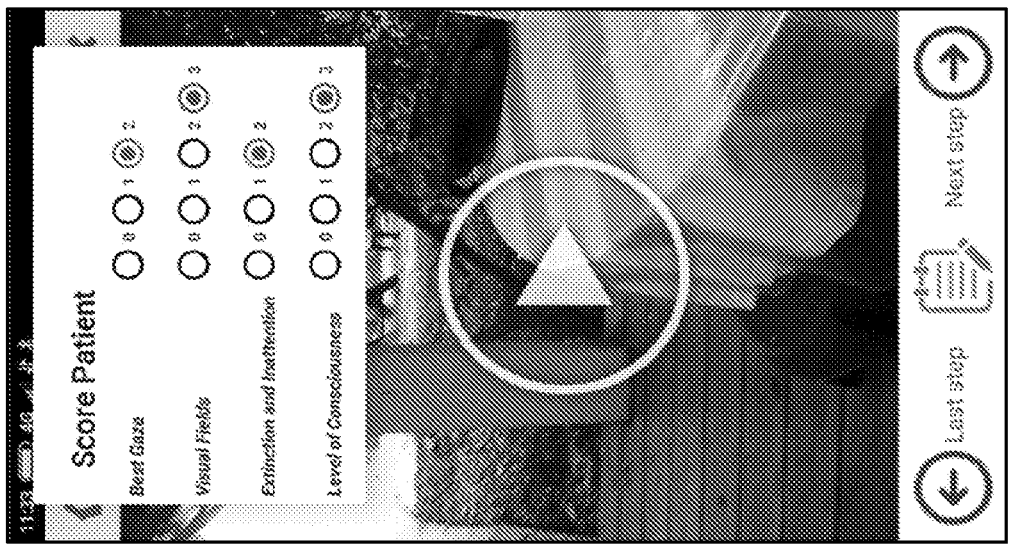
FIG. 16 is an exemplary screenshot showing a further example of individual scores of various subtests performed on the subject.

Reference is now further made to FIG. 16, which is an exemplary screenshot, generally referenced 390, showing a further example of individual scores of various subtests performed on the subject. Screenshot 390 illustrates a typical graphical user interface (GUI) that enables interactivity with a patient, and a physician.

Figure 17A:
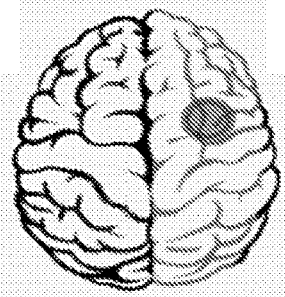
FIG. 17A is an exemplary screenshot of a system-generated stroke type and stroke location interpretation report that includes a generic brain image superimposed with a highlighted region corresponding to the location of the stroke condition, prior to neuroimaging.

Reference is now further made to FIGS. 17A and 17B. FIG. 17A is an exemplary screenshot of a system-generated stroke type and stroke location interpretation report, generally referenced 400, that includes a generic brain image superimposed with a highlighted region corresponding to the location of the stroke condition, prior to medical brain imaging. FIG. 17B is an exemplary screenshot of a system-generated stroke type and stroke location interpretation report, generally referenced 410 that includes a brain image of a subject acquired via a neuroimaging technique superimposed (e.g., fused, combined image data layers, etc.) with a highlighted region corresponding to the location stroke condition, after neuroimaging. These reports generally include summarized information as well as expanded information pertaining to the brain region (location, area, volume) of suspected brain damage during two critical phases of a stroke event based on acquired neurophysiological data (i.e., clinical measurement data from a subject), as well as after neuroimaging of the brain has been performed (e.g., via CT, fMRI, PET, etc.). Processor 104S is configured and operative to generate a stroke type and stroke location interpretation report which includes: (1) a generic image of a brain (FIG. 17A) superimposed with a highlighted region indicating at least one estimated location of the detected stroke condition ("brain damage"); (2) a brain image of a subject (FIG. 17B) superimposed with a highlighted region indicating at least one estimated location of the detected stroke condition ("brain damage"); (3) information pertaining to the stroke type (ischemic, hemorrhagic), as well as stroke sub-type (e.g., large vessel occlusion (LVO), small vessel occlusion (SVO), transient ischemic attack (TIA)); (4) brain location of stroke (e.g., M2); (5) estimated probabilities (e.g., statistics, confidence levels) pertaining to the type and location of detected possible stroke (e.g., hemorrhagic: 9.3%), ischemic M1: 14.1%, ischemic M2: 55.1%; and no stroke 21.5% (as shown in FIG. 17A); and (6) an indication of brain-hemispheric location of suspected stroke condition (e.g., left hemisphere, right hemisphere). Processors 104 and 104S and thus configured and operative include the function of a "stroke scale quantification module". Systems $101_1$ and $101_2$ are configured and operative to revise (e.g., update, modify, tweak) the probabilities to the type and location of stroke following the acquisition of a brain image from the subject (via at least one neuroimaging technique such as CT) as shown by the statistics in FIG. 17B with respect to those in FIG. 17A. FIG. 17B illustrates the following updated probabilities (statistics, confidence levels): no stroke: 2.4%; hemorrhagic: 1.2%; ischemic M1: 10.3%; and ischemic M2: 86.1%.

Figure 18:
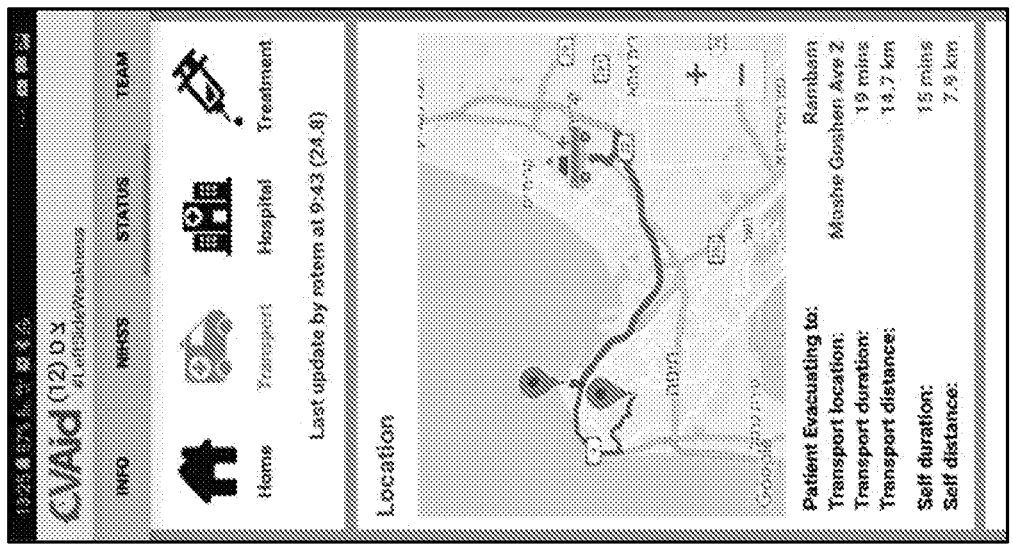
FIG. 18 is an exemplary screenshot showing an example of a stroke patient evacuation to an emergency department (ED) of a medical healthcare facility using optimization criteria and global positioning data, according to the disclosed technique.

Reference is now made to FIG. 18, which is an exemplary screenshot, generally referenced 450, showing an example of a stroke patient evacuation to an emergency department (ED) of a medical healthcare facility using optimization criteria and global positioning data, according to the disclosed technique. FIG. 18 shows an aspect of controlling and managing a stroke event (CVA) where a stroke patient is evacuated to an ED that is chosen so as to minimize commuting time thereto. Processor 104S is configured and operative (e.g., with corresponding software and/or firmware) to utilize a location determining module (e.g., a satellite-based radio-navigation receiver, such as Global Positioning System (GPS) receiver—not shown) in client device $101C_f$ so as to localize subject with respect to at least one ED in patient's vicinity, and to optimally manage the stroke event (e.g., along a medical "management pipeline"). Example management techniques employed by the disclosed technique include choosing an ED for evacuation according to optimization criteria, such as commuter-traffic considerations, relevant stroke care workforce capacity known to be in the ED, stroke-care equipment known to be in the ED, sorting a plurality of simultaneous stroke patients among different medical healthcare facilities, aiding physicians in medical decisions (e.g., interventions and operations such as brain catheterization, administration of tissue plasminogen activator (tPA)), etc. The disclosed technique provides several "decision-making configurations" to determine (e.g., quantify) a stroke scale, among which include physician only, system only (e.g., ML, without physician intervention), as well as a hybrid configuration of both physician and system interventions. Processor 104S is further configured and operative to send an automated message via communication module 108S for scheduling urgent neuroimaging of the patient (e.g., remotely scheduling a CT scan), scheduling urgent cerebral angiography of the patient, as well as automatically alerting relevant medical teams (e.g., a stroke center team, a neuro-radiologist, an intensive care team, a neuroimaging department, a telemedicine service team, a stroke "hotline" service) to prepare for the arrival of the patient, send a stroke type and stroke location interpretation report (FIG. 17A), and to guide the neuro-radiologist toward a suspected stroke location and stroke type in advance of a CT scan (so as to enable early warning and faster preparation), etc. Processor 104S is configured and operative to provide a computerized interpretation of a CT image based on the determined estimated probabilities $P_T$ and $P_L$ (i.e., probability of stroke type and probability of stroke location (respectively) with respect to either a generic brain image of the subject, or a previously acquired and database-stored CT image of the subject—not shown).

Figure 19:
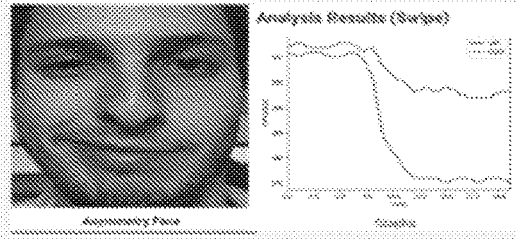
FIG. 19 is an exemplary screenshot of a system-generated stroke classification report for providing to medical personnel.

Reference is now made to FIG. 19, which is an exemplary screenshot, generally referenced 470, of a system-generated stroke classification report for providing to medical personnel. Processor 104S is configured and operative to generate a stroke classification report that includes stroke scale quantification, and to send this report via communication module 108S to at least one management console 220 for at least one medical professional, typically for medical personnel or staff. The stroke classification report may be pre-approved by a neurologist. The stroke classification report may include an estimated stroke severity (e.g., NIHSS score), the most informative image (or group of images) for "manual evaluation" of the physician (a neurologist), and a confidence level (i.e., how well the system is confident in the suggested estimation).

Another aspect of the disclosed technique involves using the infrastructure of systems $100_1$ and $100_2$ to estimate diseases, conditions, and neurological disorders other than stroke, such as Parkinson's disease, dementia, psychiatric and mental diseases, facial visual disorders, etc. Estimation to a likelihood of a variety of medical conditions can be covered by a modified version of a stroke scale described herein and/or can be covered by other medical scales, e.g., Unified Parkinson's Disease Rating Scale (UPDRS) for Parkinson's disease). For example, some symptoms of Parkinson's disease can be detected during diagnostic tests for stroke (such as the NIHSS test).

TABLE 1

| NIHSS Category | NIHSS Task | Adopted/ Modified NIHSS Computerized Test | Extraction of potential stroke features |
|---|---|---|---|
| Level of Consciousness (LOC) responsiveness | The examiner first assesses if the subject is fully alert to his/her surroundings. If the subject is not completely alert, examiner attempts a verbal stimulus to arouse the subject. Failure of verbal stimuli leads to an attempt to arouse the subjec via repeated physical stimuli. If none of these stimuli are successful in eliciting a response, the subject can be considered totally unresponsive. | Acquire and record image and sound data from subject who is instructed to provide verbal feedback when touched on both sides of body and then asked several basic questions (e.g., age, the current month). | POI and ROI extraction: Processors 104 and 104S are configured and operative to extract potential stroke features in the image data and in the sound data by detecting and extracting POI and ROI (e.g., image and voice segments of the subject voice segments of a narrator, while the subject is being touched during questioning). In case there's no feedback from the subject, the algorithm outputs the maximum score for this category. Measurements/Features extraction: Processors 104 and 104S (e.g., employing an algorithm) are configured and operative measures the response time intervals between the narrator's commands (human or synthetic) and the patient's feedback. Medical report outputs: 1) The test recordings. 2) TRUE/FASE indication for responsiveness in each test. 3) Response time interval values between the narrator's instructions and the patient's responses for each test. 4) NIHSS score—guided by the MLC. Note: MLC outputs a score according to the current NIHSS category (the classifier is pre-trained with previous analyzed subjects and their NIHSS scores as ground truth). |
| LOC questions | Subject is verbally asked his/her age and for the name of the current month. | | |

TABLE 2

| NIHSS Category | NIHSS Task | Adopted/ Modified NIHSS Computerized Test | Extraction of potential stroke features |
|---|---|---|---|
| LOC commands | The subject is instructed to first open and close his/her eyes and then grip and release his/her hand | Acquire and record images of the subject's face with sound while the subject is instructed to close and open eyes, then record subject's body while he is instructed to grip and release his hand. | POI and ROI extraction: Processors 104 and 104S are configured and operative to extract potential stroke features in the image data and in the sound data by detecting and extracting POI and ROI (e.g., image features, and voice segments of the subject patient and a narrator, while the subject is visually responding to the instructions: open-close eyes, grip-release hand. If patient feedback does not exist, the algorithm outputs the maximum score for this category. Measurements/Features extraction: Processors 104 and 104S (e.g., via an algorithm) detect and tracks the eyes in the video and also detects blinking or closing of the eyes. The algorithm measures the response time intervals between the narrator's commands (human or synthetic) and the patient's visual feedback. Another algorithm detects and tracks the hands of the patient in the video, and also detects the grip and release gestures in the video. Medical report outputs: 1) The test recordings. 2) TRUE/FALSE value for each test regarding the responsiveness. 3) Response time intervals between the narrator's instructions and the patient's responses for each test. 4) NIHSS score—guided by the MLC. 5) According to the detected region of interest: a. Cropped videos for each test. b. Cropped videos for each test with eye tracker algorithm animation/hand tracking animation. c. Snapshots from the video, for example, eyes close, eyes open, hand grip and release. Note: The MLC outputs a score according to the current NIHSS category (the classifier is pre-trained with previous analyzed subjects and their NIHSS scores as ground truth). |

TABLE 3

| NIHSS Category | NIHSS Task | Adopted/Modified NIHSS Computerized Test | Extraction of potential stroke features |
|---|---|---|---|
| Horizontal eye movement | Assesses ability of the patient to track a pen or finger from side to side only using his or her eyes. This is designed to assess the motor ability to gaze towards the hemisphere opposite to injury. | Record the patient's face with camera and microphone while he is instructed to look straight into the camera. | POI and ROI extraction: Processors 104 and 104S are configured and operative (e.g., via an algorithm) to analyze the video and voice signals and detect moments when the narrator gives the current instructions, and the moments when the patient responds to the instructions, looking straight at the camera. If patient feedback does not exist, the algorithm outputs the maximum score for this category. Measurements/Features extraction: Processors 104 and 104S are configured and operative (e.g., an algorithm) to detect and track the facial landmarks of the patient, specifically the eyes and the symmetry axis of the face. The algorithm analysis of the patient's gaze is quantified by calculating the head pose of the patient relative to the camera during this test. The algorithm measures every frame of the video, if one side of the patient's face is more gaze-deviated (relative to the camera plane) compared to the other side of his face. Medical report outputs: 1) The test recordings. 2) TRUE/FALSE value for each test regarding the responsiveness. 3) Response time intervals between the narrator's instructions and the patient's responses for each test. 4) NIHSS score—guided by the MLC. 5) According to the detected region of interest: a. Cropped videos for each test. b. Cropped videos for each test with eye tracker/facial symmetry axis algorithm animation. c. Snapshots from the video, for example, maximum gaze asymmetry frame, minimum gaze asymmetry frame. d. Eye coordination and the facial symmetry axis position for all video frames (including calculation of more measurements from these data such as variance, average speed, distance, etc.). Note: The MLC outputs a score according to the current NIHSS category (the classifier is pre-trained with previous analyzed subjects and their NIHSS scores as ground truth). |

TABLE 4

| NIHSS Category | NIHSS Task | Adopted/Modified NIHSS Computerized Test | Extraction of potential stroke features |
|---|---|---|---|
| Visual field test | Assess the patient's vision in each visual field. Each eye is tested individually, by covering one eye and then the other. Each upper and lower quadrant is tested by asking the patient to indicate how many fingers the investigator is presenting in each quadrant. | Record the patient's face with camera and microphone while he instructed to cover one of his eyes and then say the number that he sees, from a screen or by the fingers of the instructor, This test is conducted for both sides separately. | POI and ROI extraction: Processors 104 and 104S are configured and operative (e.g., via an algorithm) to analyze the video and voice signals and detects the moments when the narrator gives the current instructions, and the moments when the patient responds to the instructions, covers the eye, says the presented number, for both sides separately. If patient feedback does not exist, the algorithm outputs the maximum score for this category. Measurements/Features extraction: Processors 104 and 104S are configured and operative (e.g., via an algorithm) to detect and track the eyes of the patient. The analysis of the patient's visual field test is quantified by detecting the moments that the patient covers one of his eyes until he recognizes and says the presented number and the voice of the spoken number is analyzed. The algorithm measures the response time intervals between the narrator's commands (human or synthetic) and the patient's verbal feedback. The algorithm also analyzes the speech of the patient by trying to recognize a valid number within the voice recording. Medical report outputs: 1) The test recordings. 2) TRUE/FALSE value for each test regarding the responsiveness. 3) Response time intervals between the narrator's |

TABLE 4-continued

| NIHSS Category | NIHSS Task | Adopted/Modified NIHSS Computerized Test | Extraction of potential stroke features |
|---|---|---|---|
| | | | instructions and the patient's responses for each test.<br>4) NIHSS score—guided by the MLC.<br>5) According to the detected region of interest:<br>a. Cropped videos for each test.<br>b. Cropped videos for each test with eye tracker algorithm animation.<br>c. Snapshots from the video, for example, right eye covered, left eye covered, neutral face and face while speaking.<br>d. Eye coordination for all video frames (including calculation of more measurements from these data such as variance, average speed, distance, etc.).<br>Note: The MLC outputs a score according to the current NIHSS category (the classifier is pre-trained with previous analyzed subjects and their NIHSS scores as ground truth). |

TABLE 5

| NIHSS Category | NIHSS Task | Adopted/Modified NIHSS Computerized Test | Extraction of potential stroke features |
|---|---|---|---|
| Facial palsy | Facial palsy is partial or complete paralysis of portions of the face. Typically, this paralysis is most pronounced in the lower half of one facial side. | Record the patient's face with camera and microphone while he instructed to smile and show his teeth. | POI and ROI extraction:<br>Processors 104 and 104S are configured and operative (e.g., via an algorithm) to analyze the video and voice signals and to detect the moments when the narrator gives the current instructions, and the moments when the patient responds to the instructions, smiles and shows the teeth. If patient feedback does not exist, the algorithm outputs the maximum score for this category.<br>Measurements/Features extraction:<br>Processors 104 and 104S are configured and operative (e.g., via an algorithm) to detect and track the facial landmarks of the patient, including the patient's eyes, lips and facial symmetry axis. The analysis of the patient's facial palsy is quantified by measuring the asymmetry between correlated face part coordinates and their relative distance from the facial symmetry axis during the entire video.<br>The algorithm also measures the response time intervals between the narrator's commands (human or synthetic) and the patient's visual feedback.<br>Medical report outputs:<br>1) The test recordings.<br>2) TRUE/FALSE value for each test regarding the responsiveness.<br>3) Response time intervals between narrator's instructions and patient's responses for each test.<br>4) NIHSS score—guided by the MLC.<br>5) According to the detected region of interest:<br>a. Cropped videos for each test.<br>b. Cropped videos for each test with face tracker algorithm animation.<br>c. Snapshots from the video, for example, neutral face, most asymmetrical face, smile climax.<br>d. Face part coordinates and symmetry axis position for all video frames (including calculation of more measurements from these data such as variance, average speed, distance, etc.).<br>Note: The MLC outputs a score according to the current NIHSS category (the classifier is pre-trained with previous analyzed subjects and their NIHSS scores as ground truth). |

TABLE 6

| NIHSS Category | NIHSS Task | Adopted/Modified NIHSS Computerized Test | Extraction of potential stroke features |
|---|---|---|---|
| Motor arm | With palm facing downwards, have the patient extend one arm 90 degrees out in front if the patient is sitting, and 45 degrees out in front if the patient is lying down. | Record the patient's upper body with camera and microphone while he is instructed to lift his arms simultaneously to 90 degrees. | POI and ROI extraction: Processors 104 and 104S are configured and operative (e.g., via an algorithm) to analyze the video and voice signals and to detect the moments when the narrator gives the current instructions, and the moments when the patient responds to the instructions, lifting his hands. If patient feedback does not exist, the algorithm outputs the maximum score for this category. Measurements/Features extraction: An algorithm detects and tracks the hands of the patient; the analysis of the patient's motor arm is quantified by measuring the distance, height, and angle of each hand separately from the body. It calculated from the start of the motion to the end of the motion, and then asymmetry measurements between the hands are calculated relating to the whole video. The algorithm also measures the response time intervals between the narrator's commands (human or synthetic) and the patient's visual feedback. Medical report outputs: 1) The test recordings. 2) TRUE/FALSE value for each test regarding the responsiveness. 3) Response time intervals between the narrator's instructions and the patient's responses for each test. 4) NIHSS score-guided by the MLC. 5) According to the detected region of interest: a. Cropped videos for each test. b. Cropped videos for each test with hand tracker algorithm animation. c. Snapshots from the video, for example, neutral hands, max hand lift, most asymmetric frame between hand height. d. Hand and body distances, heights, and angles for all video frames. e. Summarizing asymmetry measurements between hands during the whole video. Note: The MLC outputs a score according to the current NIHSS category (the classifier is pre-trained with previous analyzed subjects and their NIHSS scores as ground truth). |

TABLE 7

| NIHSS Category | NIHSS Task | Adopted/Modified NIHSS Computerized Test | Extraction of potential stroke features |
|---|---|---|---|
| Motor leg | With the patient in the supine position, one leg is placed 30 degrees above horizontal, As soon as the patient's leg is in position, the investigator should begin verbally counting down from 5 while simultaneously counting down on his or her fingers in full view of the patient. Observe any downward leg drift prior to the end of the 5 seconds. | Record the patient's lower body with camera and microphone while he is instructed to lift each one of his legs separately to 30 degrees. | POI and ROI extraction: Processors 104 and 104S are configured and operative (e.g., via an algorithm) to analyze the video and voice signals and to detect the moments when the narrator gives the current instructions and the moments that the patient responds to the instructions to lift his legs. If patient feedback does not exist, the algorithm outputs the maximum score for this category. Measurements/Features extraction: An algorithm detects and tracks the legs of the patient. The analysis of the patient's motor leg is quantified by measuring the distance, height, and angle of each leg separately from the body. It calculates from the start of the motion to the end of the motion, and then asymmetry measurements between the legs are calculated relating to the whole video. The algorithm also measures the response time intervals between the narrator's commands (human or synthetic) and the patient's visual feedback. Medical report outputs: 1) The test recordings. 2) TRUE/FALSE value for each test regarding the responsiveness. 3) Response time intervals between the narrator's instructions and the patient's responses for each test. 4) NIHSS score—guided by the MLC. 5) According to the detected region of interest: |

TABLE 7-continued

| NIHSS Category | NIHSS Task | Adopted/Modified NIHSS Computerized Test | Extraction of potential stroke features |
|---|---|---|---|
| | | | a. Cropped videos for each test.<br>b. Cropped videos for each test with hand tracker algorithm animation.<br>c. Snapshots from the video, for example, neutral legs, max leg lift for each leg, most asymmetric frames between legs.<br>d. Leg and body distances, heights, and angles for all video frames.<br>e. Summarizing asymmetry measurements between legs during the whole video.<br>Note: The MLC outputs a score according to the current NIHSS category (the classifier is pre-trained with previous analyzed subjects and their NIHSS scores as ground truth). |

TABLE 8

| NIHSS Category | NIHSS Task | Adopted/Modified NIHSS Computerized Test | Extraction of potential stroke features |
|---|---|---|---|
| Limb ataxia | This tests for the presence of a unilateral cerebellar lesion, and distinguishes between general weakness and inco-ordination. The patient should be instructed to first touch his or her finger to the examiner's finger, then move that finger back to his or her nose | Record the patient's face and upper body with camera and microphone while he is instructed to touch the screen or the instructor's finger, and then touch his nose with the same finger. | POI and ROI extraction: Processors 104 and 104S are configured and operative (e.g., via an algorithm) to analyze the video and voice signals and to detect the moments when the narrator gives the current instructions, and the moments that the patient visually responds to the instructions, the first touch of his finger to instructor's finger or screen, and the second touch of the same finger with his nose. If patient feedback does not exist, the algorithm outputs the maximum score for this category.<br>Measurements/Features extraction:<br>An algorithm detects and tracks the hands and the finger used by the patient, and also detects and tracks the patient's facial landmarks, including his nose. The analysis of the patient's limb ataxia is quantified by measuring the distance and speed of motion between the finger-to-finger touching and between finger-to-nose touching during this test. The video is analyzed from the start of the motion to the end of the motion, then a total score is calculated for the patient's motion performance (success/failure/partial success) relating the whole video.<br>The algorithm also measures the response time intervals between the narrator's commands (human or synthetic) and the patient's visual feedback.<br>Medical report outputs:<br>1) The test recordings.<br>2) TRUE/FALSE value for each test regarding the responsiveness.<br>3) Response time intervals between the narrator's instructions and the patient's responses for each test.<br>4) NIHSS score—guided by the MLC.<br>5) According to the detected region of interest:<br>a. Cropped videos for each test.<br>b. Cropped videos for each test with hand tracker algorithm animation and face tracker algorithm animation.<br>c. Snapshots from the video, for example, touch between fingers, touch between finger to nose, closest point between nose and finger.<br>d. Finger-to-nose and finger-to-finger distances and speeds for all video frames.<br>e. Summarizing score measure for success failure/partial success of the touching during the whole video.<br>Note: The MLC outputs a score according to the current NIHSS category (the classifier is pre-trained with previous analyzed subjects and their NIHSS scores as ground truth). |

TABLE 9

| NIHSS Category | NIHSS Task | Adopted/Modified NIHSS Computerized Test | Extraction of potential stroke features |
|---|---|---|---|
| Language | This item measures the patient's language skills. After completing items (Tables) 1-8, it is likely the investigator has gained an approximation of the patient's language skills; however, it is important to confirm this measurement at this time The stroke scale includes a picture of a picture of a scenario, a list of simple sentences, a figure of assorted random objects, and a list of words. The patient should be asked to explain the scenario depicted in the first figure. Next, he or she should read the list of sentences and name each of the objects depicted in the next figure. | Record the patient's responses with camera and microphone while the instructor is guiding the patient to read sentences and describe a picture of several objects, which is presented to the patient on the mobile device screen. | POI and ROI extraction: Processors 104 and 104S are configured and operative (e.g., via an algorithm) to analyze the video and voice signals and to detect the moments when the narrator gives the current instructions, and the moments that the patient visually and verbally responds to the instructions, reading a sentence or naming an object from a picture. If patient feedback does not exist, the algorithm outputs the maximum score for this category. Measurements/Features extraction: An algorithm detects and tracks the patient's facial landmarks, including his mouth. The algorithm also detects the voice segments that the narrator or the patient speaks based on the mouth movement and audio signals. The analysis of the patient's language and speech is quantified by measuring the similarity between the recorded voice segments of the patient and the words and objects that are presented to him during the test. The video is analyzed from the start of the test to the end of the test, then a total score is calculated for the patient's verbal feedback (success/failure/partial success) relating to the whole video. The algorithm also measures the motion of the patient's mouth. The algorithm also measures the response time intervals between the narrator's commands (human or synthetic) and the patient's visual feedback. Medical report outputs: 1) The test recordings. 2) TRUE/FALSE value for each test regarding the responsiveness. |

TABLE 10

| NIHSS Category | NIHSS Task | Adopted/Modified NIHSS Computerized Test | Extraction of potential stroke features |
|---|---|---|---|
| Speech | Dysarthria is the lack of motor skills required to produce understandable speech. Dysarthria is strictly a motor problem and is not related to the patient's ability to comprehend speech. Strokes that cause dysarthria typically affect areas such as the anterior opercular, medial prefrontal and premotor, and anterior cingulate regions. These brain regions are vital in coordinating motor control of the tongue, throat, lips, and lungs. To perform this test, the patient is asked to read from the list of words provided with the stroke scale while the examiner observes the patient's articulation and clarity of speech. | Record the patient's responses with camera and microphone while the instructor is guiding the patient to read sentences and describe a picture of several objects, which is presented to the patient on the mobile device screen. | POI and ROI extraction: Processors 104 and 104S are configured and operative (e.g., via an algorithm) to analyze the video and voice signals and to detect the moments when the narrator gives the current instructions, and the moments that the patient visually and verbally responds to the instructions, reading a sentence or naming an object from a picture. If patient feedback does not exist, the algorithm outputs the maximum score for this category. Measurements/Features extraction: An algorithm detects and tracks the patient's facial landmarks, including his mouth. The algorithm also detects the voice segments that the narrator or the patient speaks based on the mouth movement and audio signals. The analysis of the patient's language and speech is quantified by measuring the similarity between the recorded voice segments of the patient and the words and objects that are presented to him during the test. The video is analyzed from the start of the test to the end of the test, then a total score is calculated for the patient's verbal feedback (success/failure/partial success) relating to the whole video. The algorithm also measures the motion of the patient's mouth. The algorithm also measures the response time intervals between the narrator's commands (human or synthetic) and the patient's visual feedback. Medical report outputs: 1) The test recordings. a. TRUE/FALSE value for each test regarding the responsiveness. |

TABLE 11

| NIHSS Category | NIHSS Task | Adopted/Modified NIHSS Computerized Test | Extraction of potential stroke features |
|---|---|---|---|
| Sensory | Sensory testing is performed via pinpricks in the proximal portion of all four limbs. While applying pinpricks, the investigator should ask whether or not the patient feels the pricks, and if he or she feels the pricks differently on one side when compared to the other side. | Record the patient's responses with camera and microphone while the instructor is applying pinpricks on the patient's body on both sides separately. | POI and ROI extraction: Processors 104 and 104S are configured and operative (e.g., via an algorithm) to analyze the video and voice signals and to detect the moments when the narrator speaks the current instructions, and while he touches the patient. The algorithm also analyzes the moments that the patient visually and verbally responds to the instructions and touching. If patient feedback does not exist, the algorithm outputs the maximum score for this category. Measurements/Features extraction: An algorithm detects the voice segments when the narrator asks the patient if he feels his touching. The algorithm also detects the voice feedback of the patient to the touching. The analysis of the patient's responses is quantified by analyzing the voice feedback to the touching, specifically if the feedback is positive or negative. The video is analyzed from the start of the test to the end of the test, then a total score is calculated to summarize the verbal feedback of the touching (negative/positive/partial) relating to the whole video. The algorithm also measures the response time intervals between the narrator's commands (human or synthetic) and the patient's visual feedback. Medical report outputs: 1) The test recordings. 2) TRUE/FALSE value for each test regarding the responsiveness. 3) Response time intervals between the narrator's instructions and the patient's responses for each test. 4) NIHSS score—guided by the MLC. 5) According to the detected region of interest: a. Cropped videos for each test. b. Cropped videos for each test with mouth tracker algorithm animation and the moments of answering of the patient. c. Snapshots from the video, for example, while patient is being touched. d. Summarizing score measure for negative/positive response of patient touching feedback during the whole video. Note: The MLC outputs a score according to the current NIHSS category (the classifier is pre-trained with previous analyzed subjects and their NIHSS scores as ground truth). |

TABLE 12

| NIHSS Category | NIHSS Task | Adopted/Modified NIHSS Computerized Test | Extraction of potential stroke features |
|---|---|---|---|
| Extinction and inattention | Sufficient information regarding this item may have been obtained by the examiner to properly score the patient in items 1-10. However, if any ambiguity exists, the examiner should test this item via a technique referred to as "double simultaneous stimulation". This is performed by having the patient close his or her eyes and asking him or her to identify the side on which they are being touched by the examiner. During this time, the examiner alternates between touching the patient on the right and left a sides. Next, the examiner touches the patient on both sides at the same time. This should be repeated on the patient's face, arms, and legs. To test extinction in vision, the examiner should hold up one finger in front of each of the patient's eyes and ask the patient to determine which finger is wiggling or if both are wiggling. The examiner should then alternate between wiggling each finger and wiggling both fingers at the same time. | | Note: The extinction and inattention category is covered by the other NIHSS categories described in this table (For example, see "LOC Commands" category, specifically the eyes closing test). |

After quantifying each category of the NIHSS, the total score can define the stroke severity according as follows: a score of 0 indicates no stroke symptoms; a score between 1 and 4 indicates a minor stroke; a score between 5 and 15 indicates a moderate stroke; a score between 16 and 20 indicates a moderate to severe stroke; and a score of 21-42 indicates a severe stroke. The disclosed technique is configured and operative to calculate the total severity score in a "decision-making" mode. The quantified scores can also be treated as recommendations for the physician, when the system configured to "decision support mode".

It will be appreciated by persons skilled in the art that the disclosed technique is not limited to what has been particularly shown and described hereinabove. Rather the scope of the disclosed technique is defined only by the claims, which follow.

The invention claimed is:

1. A method for quantitatively estimating a likelihood of a stroke condition of a subject, the method comprising:
acquiring non-invasive clinical measurement data pertaining to said subject, said clinical measurement data including at least one of image data, sound data, movement data, and tactile data;
constructing, via machine learning in an initial training phase, a positive stroke model from at least part of a positive stroke dataset acquired from a plurality of subjects positively diagnosed with at least one stroke condition and, in a steady-state operation phase continuously updating by training through machine learning said positive stroke model via its defining parameters through parameter estimation and optimization;
extracting from said clinical measurement data, potential stroke features according to at least one predetermined stroke assessment criterion;
comparing said potential stroke features with classified sampled data of said positive stroke dataset; and
determining, according to said comparing and said positive stroke model, without neuroimaging of said subject, a probability of a type of said stroke condition, and a probability of a corresponding stroke location of said stroke condition with respect to a particular brain location of said subject.

2. The method according to claim 1, further comprising constructing, via machine learning in said initial training phase, a negative stroke model from at least part of a negative stroke dataset acquired from a plurality of subjects negatively diagnosed with a stroke condition, and in said steady-state operation phase continuously updating by training through machine learning said negative stroke model via its defining parameters through parameter estimation and optimization, wherein said comparing is further performed on classified sampled data of said negative stroke dataset.

3. The method according to claim 2, wherein said acquiring, said extracting, said comparing, and said determining are performed for constructing a baseline profile of said subject, wherein said baseline profile defines a time-dependent estimated neurological state of said subject.

4. The method according to claim 3, further comprising comparing between at least two said baseline profiles acquired at different times to determine changes in said clinical measurement data at said different times.

5. The method according to claim 4, further comprising generating a report from comparison between said at least two said baseline profiles.

6. The method according to claim 2, wherein said comparing involves pre-configuration to enable classification of said potential stroke features to said positive stroke dataset, and to said negative stroke dataset.

7. The method according to claim 2, wherein said comparing involves pre-training via at least one machine learning classifier (MLC) to enable classification of said potential stroke features to said positive stroke dataset, and to said negative stroke dataset.

8. The method according to claim 1, further comprising preprocessing of at least part of said clinical measurement data, prior to said extracting.

9. The method according to claim 1, wherein said extraction is of at least one of a region of interest (ROI), and a point of interest (POI) in at least one of a spatial domain, and a temporal domain.

10. The method according to claim 9, wherein said comparing further involves assessing a statistical correlation between said image data, said sound data, said movement data, and said tactile data.

11. The method according to claim 1, wherein said at least one predetermined stroke assessment criterion is selected from a list consisting of:
a standardized test;
a National Institutes of Health Stroke Scale (NIHSS) test;
a face-arm-speech-time (FAST) test;
a $ABCD^2$ score;
a $CHADS_2$ score;
a $CHA_2DS_2VASc$ score;
a Los Angeles Pre-hospital Stroke Screen (LAPSS) test
a non-standardized test;
a modified test based on a standardized test;
a modified NIHSS (mNIHSS) test;
a customized test based on a standardized test; and
at least one characterizing mark.

12. The method according to claim 2, wherein said positive stroke dataset includes entries, each entry includes at least two fields: a stroke type and corresponding brain location.

13. The method according to claim 2, wherein said determining uses results outputted from said comparing that respectively represent quantitative measures indicating how extracted said stroke features match with corresponding said entries in said positive stroke dataset and entries in said negative stroke dataset.

14. The method according to claim 1, wherein said at least one positive stroke model is constructed for each of said potential stroke features.

15. The method according to claim 1, further comprising communicating information pertaining to said probability for said type of said stroke condition, and said probability of said corresponding stroke location to at least one device that is associated with at least one of said subject, a physician, and a medical facility.

16. The method according to claim 15, further comprising presenting least one of a region of interest (ROI), and a point of interest (POI) in extracted said clinical measurement data that corresponds with a highest estimated said likelihood of said stroke condition, according to determined said probability of said type of said stroke condition, and said probability of said corresponding stroke location.

17. A system for quantitatively estimating a likelihood of a stroke condition of a subject, the system comprising:
a database, containing classified sampled datasets acquired from a plurality of subjects, each positively diagnosed with at least one stroke condition, defining a positive stroke dataset; and
a processor, configured to receive non-invasive clinical measurement data pertaining to said subject, and acquired from at least one sensor that is configured to acquire at least one of image data, sound data, movement data, and tactile data pertaining to said subject, said processor configured to construct, via machine learning in an initial training phase, a positive stroke model from at least part of said positive stroke dataset and, in a steady-state operation phase, continuously update by training through machine learning said positive stroke model via its defining parameters through parameter estimation and optimization, to extract from said clinical measurement data, potential stroke features according to at least one predetermined stroke assessment criterion; to compare said potential stroke features with said classified sampled datasets; and to determine according to said positive stroke model, without neuroimaging of said subject, a probability of a type of said stroke condition, and a probability of a corresponding stroke location of said stroke condition with respect to a particular brain location of said subject.

18. The system according 17, wherein said processor is further configured to construct, via machine learning in said initial training phase, a negative stroke model from at least part of a negative stroke dataset acquired from a plurality of subjects negatively diagnosed with a stroke condition, and in said steady-state operation phase continuously updating by training through machine learning said negative stroke model via its defining parameters through parameter estimation and optimization, and to compare said potential stroke features with classified sampled data of said negative stroke dataset.

19. The system according to claim 18, wherein said processor said acquires, said extracts, said compares, and said determines is for constructing a baseline profile of said subject, wherein said baseline profile defines a time-dependent estimated neurological state of said subject.

20. The system according to claim 19, wherein said processor is further configured to compare between at least two said baseline profiles acquired at different times to determine changes in said clinical measurement data at said different times.

21. The system according to claim 20, further wherein said processor is further configured to generate a report from comparison between said at least two said baseline profiles.

22. The system according to claim 18, wherein said comparing involves pre-configuration to enable classification of said potential stroke features to said positive stroke dataset, and to said negative stroke dataset.

23. The system according to claim 18, wherein said comparing involves pre-training via at least one machine learning classifier (MLC) to enable classification of said potential stroke features to said positive stroke dataset, and to said negative stroke dataset.

24. The system according to claim 17, further wherein said processor is configured to preprocess of at least part of said clinical measurement data, prior to said extraction of said potential stroke features.

25. The system according to claim 17, wherein said extraction is of at least one of a region of interest (ROI), and a point of interest (POI) in at least one of a spatial domain, and a temporal domain.

26. The system according to claim 25, wherein said comparing further involves assessing a statistical correlation between said image data, said sound data, said movement data, and said tactile data.

27. The system according to claim 17, wherein said at least one predetermined stroke assessment criterion is selected from a list consisting of:
a standardized test;
a National Institutes of Health Stroke Scale (NIHSS) test;
a face-arm-speech-time (FAST) test;
a ABCD$^2$ score;
a CHADS$_2$ score;
a CHA$_2$DS$_2$VASc score;
a Los Angeles Pre-hospital Stroke Screen (LAPSS) test
a non-standardized test;
a modified test based on a standardized test;
a modified NIHSS (mNIHSS) test;
a customized test based on a standardized test; and
at least one characterizing mark.

28. The system according to claim 18, wherein said positive stroke dataset includes entries, each entry includes at least two fields: a stroke type and corresponding brain location.

29. The system according to claim 18, wherein said determining uses results outputted from said comparing that respectively represent quantitative measures indicating how extracted said stroke features match with corresponding said entries in said positive stroke dataset and entries in said negative stroke dataset.

30. The system according to claim 17, wherein said at least one positive stroke model is constructed for each of said potential stroke features.

31. The system according to claim 17, further comprising a communication module enabled for communication with said processor, said communication module is configured to communicate information pertaining to said probability for said type of said stroke condition, and said probability of said corresponding stroke location to at least one device that is associated with at least one of said subject, a physician, and a medical facility.

32. The system according to claim 17, further including a user interface configured to interface between said system and at least one of said subject, an operator of said system, a manager of said system, and a physician using said system.

33. The system according to claim 32, wherein said user interface is configured to provide an indication to at least one of said probability of said stroke type, and said probability of said corresponding stroke location.

34. The system according to claim 33, wherein said user interface is configured to present at least one of a region of interest (ROI), and a point of interest (POI) in extracted said clinical measurement data that corresponds with a highest estimated said likelihood of said stroke condition, according to determined said probability for said type of said stroke condition, and said probability of said corresponding stroke location.

35. A system for quantitatively estimating a likelihood of a stroke condition of a subject, the system comprising:
a client device including:
at least one sensor, configured to acquire at least one of image data, sound data, movement data, and tactile data, all of which constitute non-invasive clinical measurement data pertaining to said subject;
a user interface, configured to provide an indication of a probability for a type of said stroke condition, and a probability of a corresponding stroke location of said stroke condition with respect to a particular brain location of said subject, without neuroimaging of said subject; and
a communication module, enabled for communication with a remote computer, said communication module configured to send said clinical measurement data to said remote computer, and to receive from said remote computer said indication;
wherein said indication is based on a comparison between potential stroke features extracted from said clinical measurement data according to at least one predetermined stroke assessment criterion, with classified sampled data in a database acquired from a plurality of subjects, each positively diagnosed with at least one stroke condition, defining a positive stroke dataset, and based on a positive stroke model constructed via machine learning in an initial phase from at least part of said positive stroke dataset that is in a steady-state operation phase continuously updated by training machine learning via its defining parameters through parameter estimation and optimization.

36. The system according 37, wherein said remote computer includes a processor that is configured to compare said potential stroke features with classified sampled data acquired from a plurality of subjects negatively diagnosed with a stroke condition, defining a negative stroke dataset, based on a negative stroke model constructed via machine learning in said initial training phase from at least part of said negative stroke dataset that is in said steady-state operation phase continuously updated by training through machine learning via its defining parameters through parameter estimation and optimization.

37. The system according to claim 36, wherein said remote computer is configured to construct a baseline profile of said subject, wherein said baseline profile defines a time-dependent estimated neurological state of said subject.

38. The system according to claim 37, wherein said processor is further configured to compare between at least two said baseline profiles acquired at different times to determine changes in said clinical measurement data at said different times.

39. The system according to claim 38, further wherein said processor is further configured to generate a report from comparison between said at least two said baseline profiles.

40. The system according to claim 36, wherein said comparing involves pre-configuration to enable classification of said potential stroke features to said positive stroke dataset, and to said negative stroke dataset.

41. The system according to claim 36, wherein said comparing involves pre-training via at least one machine learning classifier (MLC) to enable classification of said potential stroke features to said positive stroke dataset, and to said negative stroke dataset.

42. The system according to claim 36, said processor is configured to preprocess of at least part of said clinical measurement data, prior to said extraction of said potential stroke features.

43. The system according to claim 36, wherein said extraction is of at least one of a region of interest (ROI), and a point of interest (POI) in at least one of a spatial domain, and a temporal domain.

44. The system according to claim 43, wherein said comparing further involves assessing a statistical correlation between said image data, said sound data, said movement data, and said tactile data.

45. The system according to claim 35, wherein said at least one predetermined stroke assessment criterion is selected from a list consisting of:

a standardized test;
a National Institutes of Health Stroke Scale (NIHSS) test;
a face-arm-speech-time (FAST) test;
a $ABCD^2$ score;
a $CHADS_2$ score;
a $CHA_2DS_2VASc$ score;
a Los Angeles Pre-hospital Stroke Screen (LAPSS) test
a non-standardized test;
a modified test based on a standardized test;
a modified NIHSS (mNIHSS) test;
a customized test based on a standardized test; and
at least one characterizing mark.

46. The system according to claim 36, wherein said positive stroke dataset includes entries, each entry includes at least two fields: a stroke type and corresponding brain location.

47. The system according to claim 36, wherein said determining uses results outputted from said comparing that respectively represent quantitative measures indicating how extracted said stroke features match with corresponding said entries in said positive stroke dataset and entries in said negative stroke dataset.

48. The system according to claim 35, wherein said at least one positive stroke model is constructed for each of said potential stroke features.

49. The system according to claim 36, wherein said communication module is configured to communicate information pertaining to said probability for said type of said stroke condition, and said probability of said corresponding stroke location to at least one device that is associated with at least one of said subject, a physician, and a medical facility.

50. The system according to claim 35, wherein said user interface is configured to interface between said system and at least one of said subject, an operator of said system, a manager of said system, and a physician using said system.

51. The system according to claim 36, wherein said user interface is configured to provide an indication to at least one of said probability of said stroke type, and said probability of said corresponding stroke location.

52. The system according to claim 51, wherein said user interface is configured to present at least one of a region of interest (ROI), and a point of interest (POI) in extracted said clinical measurement data that corresponds with a highest estimated said likelihood of said stroke condition, according to determined said probability of said type of said stroke condition, and said probability of said corresponding stroke location.

* * * * *